(12) United States Patent
Davis, Jr.

(10) Patent No.: US 7,709,635 B2
(45) Date of Patent: May 4, 2010

(54) BORONIUM-ION-BASED IONIC LIQUIDS AND METHODS OF USE THEREOF

(75) Inventor: James H. Davis, Jr., Mobile, AL (US)

(73) Assignee: University of South Alabama, Mobile, AL (US)

( * ) Notice: Subject to any disclaimer, the term of this patent is extended or adjusted under 35 U.S.C. 154(b) by 511 days.

(21) Appl. No.: 11/437,417

(22) Filed: May 19, 2006

(65) Prior Publication Data

US 2006/0287521 A1   Dec. 21, 2006

Related U.S. Application Data

(60) Provisional application No. 60/682,622, filed on May 19, 2005.

(51) Int. Cl.
*C07F 5/02* (2006.01)
(52) U.S. Cl. .................. 540/541; 544/69; 544/229; 546/13; 548/110
(58) Field of Classification Search ............... 540/541; 544/69, 229; 546/13; 548/110
See application file for complete search history.

(56) References Cited

U.S. PATENT DOCUMENTS

| | | | |
|---|---|---|---|
| 2,655,524 A | | 10/1953 | Sowa |
| 3,265,737 A | * | 8/1966 | Miller .................. 564/8 |
| 3,336,380 A | | 8/1967 | Muetterties |
| 5,827,602 A | | 10/1998 | Koch et al. |
| 7,053,232 B2 | | 5/2006 | Moulton |
| 7,297,289 B2 | | 11/2007 | Sato et al. |
| 7,378,194 B2 | | 5/2008 | Michot et al. |
| 2004/0007693 A1 | | 1/2004 | Moulton |
| 2005/0081370 A1 | | 4/2005 | Kurihara et al. |
| 2006/0124902 A1 | | 6/2006 | Ziegler |

OTHER PUBLICATIONS

Frankel et al. "Homoleptic carbene complexes* Part IX. Bis(imidazolin-2-ylidene-1-yl)borate complexes of palladium(II), platinum(II) and gold(I) " Inorganica Chimica Acta, 2001, pp. 23-39.*
Fox, P. A. et al., "Exploiting isolobal relationships to create new ionic liquids: novel room-temperature ionic liquids based upon (N-alkylimidazole)(amine)BH2+ "boronium" ions," *Chem. Comm.*, 29:3679-3681 (2005).
Frankel, R. et al., "Homoleptic carbene complexes. Part IX. Bis(imidaizolin-2-ylidene-1-yl)borate complexes of palladium(II), platinum(II) and gold(I)", *Inorganica Chemica Acta*, 312:23-29 (2001).
Holley, W. K. et al., "Synthesis and characterization of the first borane adducts and boron cations of some N-alkyl and N-aminotriphenylphosphoranimines", *Database Chemical Absrtracts Service*, Database accession No. 114:42900 and *Phosphorus, Sulfur and Silocon and the Related Elements*, 53:1-4 (1990).
Mathur, Milap A. et al., "Mixed-Tris(amine) Cations of Boron and Formation Mechanism", *Inorg. Chem.*, 19(10):3054-3057 (1980).
Zaidi, S. A. A. et al., "Synthesis of dihydrobis(2-methylimidazolyl)borate anion and its chelating properties towards few transition metal ions", *Database, Chemical Abstract Service*, Database accession No. 101:239288, and *Bulletin de la Societe Chimique de France*, 5-6(1):149-152 (1984).
International Search Report dated Oct. 18, 2006.
Ryschkewitsch, G.E. et al., "On the Exchange of Trimethylamine with Trimethylamine-Borane in Benzene. A Caveat Concerning the Interpretation of Nuclear Magnetic Resonance Data," J. Am. Chem. Soc. 1970, 92(3), 745-746.
Nainan, K.C. et al., "Cations Derived from $BH_2^+$. Unsymmetrical Bis-Amine Substitution on Boron," J. Am. Chem. Soc. 1969, 91(2), 330-336.
Ryschkewitsch, G.E. "Boron Cation Homomorphs of Norborane," J. Am. Chem. Soc. 1969, 91(23), 6535-6536.
Ryschkewitsch, G.E. et al., "An Optically Active Boron Cation," J. Am. Chem. Soc. 1967, 89(16), 4240-4241.
Ryschkewitsch, G.E. "Bis(pyridine)boronium Salts. Syntheses and Formation Kinetics" J. Am. Chem. Soc. 1967, 89(13), 3145-3148.
Zutshi, K. et al., "Structural Effects on Polarographic Reduction of Substituted Dihydro(dimethylamine)(pyridine)boron(1+) Cations in Acetonitrile," Inorg. Chem. 1983, 22, 564-566.
Gragg, B.R. et al., "Synthesis of a New Class or Boron Cations from 4-Iodo-1,1,3,3-tetramethyl-1,3-diazonia-2,4-diboratocyclopentane," Inorg. Chem. 1976, 15, 1205-1209.
Ryschkewitsch, G.E. et al., "Boron Cations Derived from Diamines, Linear, Cyclic, Bicyclic 1+, and 2+ Ions and Polynuclear Species," Inorg. Chem. 1970, 9, 899-904.
Ryschkewitsch, G.E. et al., "A Cation Derived from $BH_2^+$ and Acetonitrile," Inorg. Chem. 1970, 9, 411-412.
Nainan, K.C. et al., "A New Synthesis of Amine- and Phosphine-Boranes," Inorg. Chem. 1969, 8, 2671-2674.
Nainan, K.C. et al., "Bis-Amine Derivatives of $BH_2^+$ with Methylpyridines," Inorg. Chem. 1968, 7, 1316-1319.
Mokosky, C.W. et al.,"The Synthesis of Some Compounds Containing Divalent and Trivalent Boron Cations," Inorg. Chem. 1967, 6, 1972-1974.
Mathur, M.A. et al., "Tris(amine) Cations of Boron," Inorg. Chem. 1980, 19, 887-891.
Miller, N. E. et al., "Chemistry of Boranes. X. Borane Cations, $H_2B(base)_2^+$," J. Am. Chem. Soc. 1964, 86, 1033-1038.
Miller, N. E. et al., "Chemistry of Boranes. XVII. Pyrolysis of $H_2B(NR_3)_2^+X^-$ Salts," Inorg. Chem. 1964, 3, 1064-1065.

(Continued)

*Primary Examiner*—Joseph R Kosack
(74) *Attorney, Agent, or Firm*—Dana M. Gordon; Foley Hoag LLP

(57) ABSTRACT

One aspect of the present invention relates to "boronium" ions that are stable, hydrophobic, room-temperature ionic liquids. In certain embodiments, ionic liquids of the instant invention are represented by the formula $[X_nBY_{4-n}]^{+(n-1)}(n-1)Z^{-1}$, wherein X refers to a Lewis base, Y refers to a substituent covalently bonded to boron, $Z^{-1}$ is a charge diffuse anion, and x is 2, 3 or 4. In certain embodiments, the ionic liquids of the instant invention are of the general type $[X_2BY_2]^{+1}Tf_2N^{-1}$, wherein each X is independently a tertiary amine, a N-alkylimidazole or a pyridine; and each B—X bond is a B—N bond.

40 Claims, 12 Drawing Sheets

OTHER PUBLICATIONS

McBreen, J. et al., "New approaches to the design of polymer and liquid electroytes for lithium batteries," Journal of Power Sources 2000, 89, 163-167.

Douglass, J.E. et al., "Heterocyclic Boronium Ions. The Reactions of Diamine Salts with Sodium Borohydride," J. Org. Chem. 1969, 34, 3666-3667.

Douglass, J.E. "Bisamine Complexes of Boronium Ions. The Reaction of Amine Boranes with Iodine," J. Am. Chem. Soc. 1964, 86, 5431-5433.

Douglass, J.E. "Bisamine Complexes of Boronium Ions. The Reaction of Iodine with Pyridine Phenylborane," J. Am. Chem. Soc. 1962, 84, 121-122.

Davis Jr., J.H. et al., "Synthesis and Computational Evaluation of a Boronium Ion Analogue of the Tropane Ring System," Tetrahedron Lett. 1996, 37, 2729-2730.

\* cited by examiner

Crystal structure of above salt:

Crystal structure of above salt:

Crystal structure of above salt:

BORONIUM-ION-BASED IONIC LIQUIDS AND METHODS OF USE THEREOF

RELATED APPLICATIONS

This application claims the benefit of priority to U.S. Provisional Patent Application Ser. No. 60/682,622, filed May 19, 2005, the specifications of which is hereby incorporated in its entirety.

GOVERNMENT SUPPORT

This research has been partially funded by the U.S. Environmental Protection Agency's STAR program through grant number RD-83143201-0. Therefore, the government has certain rights in the invention.

BACKGROUND OF THE INVENTION

As recently as five years ago most chemists had never heard of ionic liquids (IL). But since then interest in these unorthodox materials has grown at a phenomenal rate. R. D. Rogers and K. R. Seddon, in *Ionic Liquids as Green Solvents-Progress and Prospects*, ed. By R. D. Rogers and K. R. Seddon, ACS Symp. Ser. 856, ACS, Washington, D.C., 2003, p. xiii. The scope of demonstrated or proposed applications of IL is extraordinary, ranging from their use as non-volatile, non-flammable solvents to advanced heat transfer fluids, lubricants and anti-statics. M. Freemantle *Chem. Eng. News* 2004, 82(45), 44; and M. Freemantle *Chem. Eng. News* 2004, 82(18), 26. Surpassing in magnitude the number of potential uses is the number of possible IL compositions, estimated by Seddon to be in the billions. K. R. Seddon, in *The International George Papatheodorou Symposium: Proceedings*, S. Boghosian, V. Dracopoulos, C. G. Kontoyannis and G. A. Voyiatzis, Eds.; Institute of Chemical Engineering and High Temperature Chemical Processes: Patras, 1999; p 131.

Ionic Liquids. Ionic liquids consist of ions. However, unlike conventional molten salts (for example, molten sodium chloride), ionic liquids often melt below 100° C. When an ionic liquid has a melting point below room temperature, it is said to be a room-temperature ionic liquid. Since their melting points are low, room-temperature ionic liquids can act as reaction solvents. Because an ionic liquid is made of ions rather than molecules, they often provide distinct selectivities and reactivities as compared to conventional organic solvents.

Room-temperature ionic liquids have been used as clean solvents and catalysts for green chemistry and as electrolytes for batteries, photochemistry and electro-synthesis. They have no significant vapor pressure and thus create no volatile organic contaminants. They also allow for easy separation of organic molecules by direct distillation without loss of the ionic liquid. Their liquid range can be as large as 300° C. allowing for large reaction kinetic control, which, coupled with their good solvent properties, allows small reactor volumes to be used. Salts based upon poor nucleophilic anions, such as $[BF_4]^-$, $[PF_6]^-$, $[CF_3CO_2]^-$, and $[CF_3SO_3]^-$, are water and air insensitive and possess remarkably high thermal stability. Many of these materials are based around an imidazolium cation, 1-alkyl-3-methylimidazolium. By changing the anion or the alkyl chain on the cation, a wide variation in properties, such as hydrophobicity, viscosity, density and solvation, can be obtained. For example, ionic liquids will dissolve a wide range of organic molecules to an appreciable extent, the solubility being influenced by the nature of the counter anion.

The unique physical properties of ionic liquids have been found to offer certain advantages in numerous applications. For example, U.S. Pat. No. 5,827,602 to Koch et al. discloses ionic liquids having improved properties for application in batteries, electrochemical capacitors, catalysis, chemical separations, and other uses. The ionic liquids described in Koch et al. are hydrophobic in nature, being poorly soluble in water, and contain only non-Lewis acid anions. When fluorinated, they were found to be particularly useful as hydraulic fluids and inert liquid diluents for highly reactive chemicals. In addition, ionic liquids have been discussed by Freemantle, M. *Chem. Eng. News* 1998, 76 [March 30], 32; Carmichael, H. *Chem. Britain* 2000, [January], 36; Seddon, K. R. *J. Chem. Tech. Biotechnol.* 1997, 68, 351; Welton, T. *Chem. Rev.* 1999, 99, 2071; Bruce, D. W., Bowlas, C. J., Seddon, K. R. *Chem. Comm.* 1996, 1625; Merrigan, T. L., Bates, E. D., Dorman, S. C., Davis, J. H. *Chem. Comm.* 2000, 2051; Freemantle, M. *Chem. Eng. News* 2000, 78 [May 15], 37; Holbrey, J. D., Seddon, K. R. *Clean Products and Processes* 1999, 1, 223-236; and Dupont, J., Consorti, C. S. Spencer, J. *J. Braz. Chem. Soc.* 2000, 11, 337-344.

Ionic liquids have been used as solvents for a broad spectrum of chemical processes. These ionic liquids, which in some cases serve as both catalyst and solvent, are attracting increasing interest from industry because they promise significant environmental benefits, e.g., because they are non-volatile they do not emit vapors. Hence, for example, they have been used in butene dimerization processes. WO 95/21871, WO 95/21872 and WO 95/21806 relate to ionic liquids and their use to catalyze hydrocarbon conversion reactions, such as polymerization and alkylation reactions. The ionic liquids described for this process were preferably 1-($C_1$-$C_4$alkyl)-3-($C_6$-$C_{30}$ alkyl) imidazolium chlorides and especially 1-methyl-3-$C^{10}$ alkyl-imidazolium chloride, or 1-hydrocarbyl pyridinium halides, where the hydrocarbyl group is, for example, ethyl, butyl or other alkyl. PCT publication WO 01/25326 to Lamanna et al. discloses an antistatic composition comprising at least one ionic salt consisting of a nonpolymeric nitrogen onium cation and a weakly coordinating fluoroorganic anion, the conjugate acid of the anion being a superacid, in combination with thermoplastic polymer. The composition was found to exhibit good antistatic performance over a wide range of humidity levels.

However, it has been pointed out that touting the environmental benefits of IL chemistry is something that should be done with care. J. D. Holbrey, M. B. Turner and R. D. Rogers in *Ionic Liquids as Green Solvents-Progress and Prospects*; R. D. Rogers and K. R. Seddon, Eds.; ACS Symposium Series 856; American Chemical Society: Washington, D.C. 2003; 2. In a recent paper, a commentary has been offered on this situation as it pertains to fluorous anions, which are the most widely used anion type in IL formulations. R. P. Swatlowski, J. D. Holbrey and R. D. Rogers *Green Chem.* 2003, 5, 361. While there are situations in which IL with fluorous anions will remain indispensable, there is much to be desired in identifying other (preferably innocuous) ions in formulating IL, especially for large-volume applications. J. H. Davis, Jr. and P. A. Fox *Chem. Commun.* 2003, 1209; R. P. Swatlowski, J. D. Holbrey and R. D. Rogers *Green Chem.* 2003, 5, 361. To this end, non-toxic organoanions such as acetate and lactate have been used to formulate IL. M. J. Earle, P. B. McCormac and K. R. Seddon, *Green Chem.* 1999, 1, 23. However, carboxylates are basic, readily engage in hydrogen bonding, and are strongly coordinating towards transition-metal ions. Such attributes are not typical of the fluorous anions on which so many IL compositions are based. Mapped onto an IL, these properties are likely to be useful in some circumstances and detrimental in others.

Brönsted Acid Catalysis. From undergraduate laboratories to chemical manufacturing plants, the use of strong Brönsted acids is ubiquitous. Smith, M. B.; March, J. *March's Advanced Organic Chemistry*; Wiley-Interscience: New York, 2001; Chapter 8. In this context, solid acids are being more widely used since, as non-volatile materials, they are deemed less noxious than traditional liquid acids. Ritter, S. K *Chem. Eng. News* 2001, 79 (40), 63-67. However, solid acids have shortcomings. Among the more troublesome of these are restricted accessibility of the matrix-bound acidic sites, high mw/active site ratios, and rapid deactivation from coking. Ishihara, K.; Hasegama, A. and Yamamoto, H. *Angew. Chem. Int. Ed.* 2001, 40, 4077-4079; and Harmer, M. A. and Sun, Q. *Appl. Catal. A: General* 2001, 221, 45-62.

Bearing in mind both the advantages and disadvantages of solid acids, the search continues for systems that are Brönsted acids with solid-like non-volatility but which manifest the motility, greater effective surface area and potential activity of a liquid phase. Combining just these characteristics, ionic liquids have been described as one of the most promising new reaction mediums. Seddon, K. R. *J. Chem. Technol. Biotechnol.* 1997, 68, 351-356. Not only can these unusual materials dissolve many organic and inorganic substrates, they are also readily recycled and are tunable to specific chemical tasks. Bates, E. D.; Mayton, R. D.; Ntai, I. and Davis, J. H. Jr. *J. Am. Chem Soc.* 2002, 124, 926-927; Visser, A. E.; Holbrey, J. D.; Rogers, R. D. *Chem. Commun.*, 2001, 2484-2485; Visser, A. E.; Swatloski, R. P.; Reichert, W. M.; Mayton, R.; Sheff, S.; Wierzbicki, A.; Davis, J. H. Jr.; Rogers. R. D. *Chem. Commun.*, 2001, 135-136; Merrigan, T. L.; Bates, E. D.; Dorman; S. C.; Davis, J. H. Jr. *Chem. Commun.* 2000, 2051-2052; Forrester, K. J.; Davis, J. H. Jr. *Tetrahedron Letters*, 1999, 40, 1621-1622; and Morrison, D. W.; Forbes D. C.; Davis, J. H. Jr. *Tetrahedron Letters*, 2001, 42, 6053-6057.

Further, the chemical industry is under significant pressure to replace the volatile organic compounds that are currently used as solvents in organic synthesis. Many of these solvents, such as chlorinated hydrocarbons, are toxic and hazardous for the environment, due to their emissions in the atmosphere and the contamination of aqueous effluents. Ionic liquids seem to offer a solution to this problem, too. Ionic liquids have no measurable vapor pressure. This means that they don't evaporate, and therefore they emit no hazardous vapors in the atmosphere, and replenishing of the solvent is not required. This property also allows easy separation of volatile products. Ionic liquids are able to dissolve a wide range of organic, inorganic and organometallic compounds. Notably, their properties can be adjusted by altering the cation or anion of the IL, allowing for fine tuning of the reaction.

Moreover, many organic transformations, such as Fischer esterification, alcohol dehydrodimerization and the pinacol/benzopinacol rearrangement, require an acidic catalyst. Solid acids are now being used, because, as nonvolatile compounds, they are less hazardous than traditional liquid acids. As noted above, although they are less hazardous, solid acids have several disadvantages, such as restricted accessibility of the matrix-bound acidic sites, high molecular weight/active-site ratios, and rapid deactivation from coking. Cole, A. C.; Jensen, J. L.; Ntai, I.; Tran, K. L. T.; Weaver, K. J.; Forbes, D. C.; Davis, J. H., Jr. *J. Am. Chem. Soc.* 2002, 124, 5962-5963.

Purification of Gas Mixtures. There is little doubt that petroleum, coal and natural gas will continue to be the primary global fuel and chemical feedstock sources for some years to come. Natural gas is regarded as the cleanest of these materials, and as such is being consumed at an accelerating pace. Despite its reputation as a clean fuel, natural gas is usually contaminated with a variety of undesirable materials, especially $CO_2$ and $H_2S$. While this level of contamination is very low in gas from certain sources (sweet gas), it is much higher in gas from others (sour gas). As sweet gas reserves are depleted, pressures will build for the increased utilization of sour gas. *Oil and Gas R&D Programs: Securing the U.S. Energy, Environmental and Economic Future*. Office of Fossil Energy, U.S. Dept. of Energy, Office of Natural Gas and Petroleum Technology: Washington, D.C., 1997. Since admixed $CO_2$ lowers the fuel value of natural gas, the large amount of it present in sour gas compels its removal prior to combustion. The lower fuel value for sour gas, coupled with the connection between $CO_2$ and global warming, makes $CO_2$ capture a commercially important and environmentally desirable process.

One of the most attractive approaches for the separation of a target compound from a mixture of gases in a gas stream is selective absorption into a liquid. Astarita, G,; Savage, D. W.; Bisio, A. *Gas Treating with Chemical Solvents*; Wiley-Interscience: New York, 1983. Such interactions between gases and pure liquids or solutions are the bases for numerous gas separation technologies, including commercial systems for the removal of $CO_2$ from natural gas. These scrubbing processes include ones in which the simple, differential dissolution of the target gas into the liquid phase is of principal importance. More common are processes in which a chemical reaction of the target gas with a solute in the liquid phase is the main mode of sequestration. With either mode of gas removal, the vapor pressure of the solvent itself plays a significant role in gas-liquid processes, usually to their detriment. In the case of large-scale $CO_2$ capture, aqueous amines are used to trap chemically the $CO_2$ by way of ammonium carbamate formation. In these systems, the uptake of water into the gas stream is particularly problematic. Compounding the water uptake difficulty is the loss into the gas stream of the volatile amine sequestering agent.

A liquid that could facilitate the sequestration of gases without concurrent loss of the capture agent or solvent into the gas stream should prove to be a superior material in such applications. To this end, ionic liquids (low temperature molten salts) have been proposed as solvent-reagents for gas separations. Pez, G. P. et al. U.S. Pat. No. 4,761,164. Due to the coulombic attraction between the ions of these liquids, they exhibit no measurable vapor pressure up to their thermal decomposition point, generally greater than 300° C. This lack of vapor pressure makes these materials highly attractive for gas processing. Indeed, for these purposes they may be thought of as "liquid solids," incorporating some of the most useful physical properties of both phases.

Despite the general promise of ionic liquids in gas treatment, the molten salts used thus far for $CO_2$ separation are generally "off the shelf" materials, such as $(CH_3)_4NF$ tetrahydrate, that are not optimized for this purpose, frequently depending upon another volatile reagent, water. Pez, G. P. et al. U.S. Pat. Nos. 4,761,164 and 4,973,456; and Quinn, R.; Appleby, J. B.; Pez, G. P. *J. Am. Chem. Soc.*, 1995, 117, 329. For instance, the latter salt uses the very weakly basic bifluoride ion to drive the net generation of bicarbonate from $CO_2$ and water.

Electrolytic Solutions. An ionic compound generally forms crystals in which positively charged cations and negatively charged anions pull electrostatically against each other. When this ionic compound is dissolved in various other liquids, including water, it provides a liquid that carries electricity; that is, an electrolyte solution. Electrolyte solutions obtained by dissolving an ionic compound in an organic solvent are commonly used in, for example, nonaqueous electrolyte batteries and capacitors.

The chemical species present in the ionic liquids are all charged cations or anions; no neutral atoms or molecules are present. Therefore, elements which cannot be obtained from an aqueous electrolyte solution because they have too large a reducing or oxidizing power with respect to water, including metals such as alkali metals, aluminum and rare-earth elements, and non-metals such as fluorine, can be electrolyzed in a ionic liquid and obtained in elemental form. This has become a main industrial application of molten salts.

Research is actively being pursued on applications for such ionic liquids in electrolytic deposition and in electrolytes for batteries and other purposes. However, because ionic liquids generally have a high moisture absorption and are difficult to handle in air, such applications has yet to be fully realized. In light of these circumstances, one aspect of the invention is to provide ionic liquids which can be easily and efficiently produced; electrolyte salts for electrical storage devices which have excellent solubility in organic solvents for nonaqueous electrolyte solutions and have a low melting point; liquid electrolytes for electrical storage devices which include these electrolyte salts; and electrical double-layer capacitors and secondary batteries of excellent low-temperature properties which are constructed using such liquid electrolytes.

Future Outlook. The prospects for preparing a broad array of ionic liquids with ions incorporating functional groups are good. Moreover, certain of these new "task-specific" ionic liquids have proven useful in both synthetic and separations applications. Visser, A. E.; Holbrey, J. D.; Rogers, R. D. *Chem. Commun.*, 2001, 2484; Visser, A. E.; Swatloski, R. P.; Reichert, W. M.; Mayton, R.; Sheff, S.; Wierzbicki, A.; Davis, J. H. Jr.; Rogers. R. D. *Chem. Commun.*, 2001, 135; Merrigan, T. L.; Bates, E. D.; Dorman; S. C.; Davis, J. H. Jr. *Chem. Commun.* 2000, 2051; Fraga-Dubreuil, J.; Bazureau J. P. *Tetrahedron Lett.*, 2001, 42, 6097; and Forrester, K. J.; Davis, J. H. Jr. *Tetrahedron Lett.*, 1999, 40, 1621.

In the absence of predictive computational methods to direct their design, the discovery-based development of new IL will remain vital to the field. This is especially the case vis-à-vis heretofore unknown or unused classes of ions when such entities are easily prepared and provide access to potentially unique structural or electronic attributes. E. B. Carter, S. L. Culver, P. A. Fox, R. D. Goode, I. Ntai, M. D. Tickell, R. K. Traylor, N. W. Hoffman and J. H. Davis, Jr. *Chem. Commun.* 2004, 630. In light of these considerations we disclose herein that an obscure cation type—the "boronium" ion—is a versatile platform for creating hydrophobic, room-temperature ionic liquids.

SUMMARY OF THE INVENTION

Herein we disclose that the "boronium" ion is a versatile platform for creating stable, hydrophobic, room-temperature ionic liquids with unique electronic and spectroscopic characteristics. In certain embodiments, ionic liquids of the instant invention may be represented by the formula $[X_nBY_{4-n}]^{+(n-1)}(n-1)Z^{-1}$, wherein X refers to a Lewis base, Y refers to a substituent covalently bonded to boron, $Z^{-1}$ is a charge diffuse anion, and x is 2, 3 or 4. In certain embodiments, the ionic liquids of the instant invention are of the general type $[X_2BY_2]^{+1}Tf_2N^{-1}$ wherein each X is a either a tertiary amines or a N-alkylimidazoles.

DETAILED DESCRIPTION OF THE INVENTION

Figure 1:
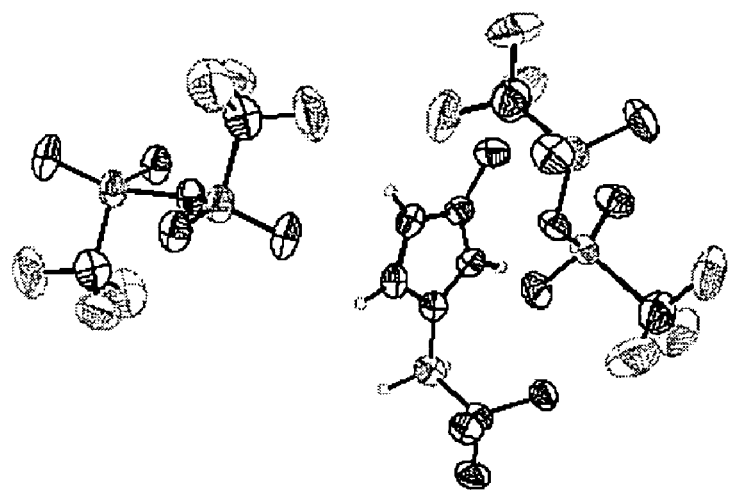
FIG. 1 depicts an ORTEP of [(N-1-methylimidazole)(trimethylamine)$BH_2]^{+1}Tf_2N^{-1}$ 1 showing the boronium cation and disordered anion set.

The invention will now be described more fully with reference to the accompanying examples, in which certain preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Definitions. For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "ionic liquid" or "IL" as used herein means an organic salt or hydrate thereof with a melting point less than about 150° C. In a preferred embodiment, the ionic liquid has a melting point of less than about 100° C. In a preferred embodiment, the ionic liquid has a melting point of less than about 50° C. In a preferred embodiment, the ionic liquid has a melting point of less than about room temperature. The ionic liquids of the present invention may comprise one or more compounds. Thus, the ionic liquid may be a pure compound or may be a mixture of compounds. Each compound comprises an anion or a mixture of anions; and a cation or a mixture of cations.

The term "boronium ion" as used herein is used to describe ions of the type $[L_xBR_{4-x}]^{(x-1)+}$, wherein L refers to a Lewis base, R refers to a substituent covalently bonded to boron, and x is 2, 3 or 4. In other words, as used herein "boronium" refers to a boron complex which has an overall net positive charge. K. C. Nainan and G. E. Ryschkewitsch *Inorg. Chem.* 1968, 7, 1316; and J. E. Douglass *J. Am. Chem. Soc.* 1962, 84, 121).

The term "Lewis base" as used herein is a substance which acts as an electron pair donor.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (a) constant. This well known constant is described in many references, for instance, J. March, *Advanced Organic Chemistry*, McGraw Hill Book Company, New York, (1977 edition) pp. 251-259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "charge-diffuse anion" as used herein is a non-Lewis acid containing polyatomic anion having a van der Waals volume exceeding 100 Å$^3$. Charge-diffuse anions include, for example, boron tetrafluoride, boron tetraphenyl, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide or bis(p-toluenesulfonyl)amide.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "bicyclo-ring" as used herein refers to a bridged ring system such as a quinuclidine (shown below).

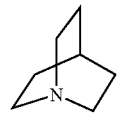

The term "aralkyl" is art-recognized, and includes alkyl groups substituted with an aryl group (e.g., an aromatic or heteroaromatic group).

The terms "alkenyl" and "alkynyl" are art-recognized, and include unsaturated aliphatic groups analogous in length and possible substitution to the alkyls described above, but that contain at least one double or triple bond respectively.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "aryl" is art-recognized, and includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho (o-), meta (m-) and para (p-) are art-recognized and apply to 1,2-, 1,3- and 1,4-disubstituted benzenes, respectively. For example, the names 1,2-dimethylbenzene, ortho-dimethylbenzene and o-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, fluoroalkyl (such as trifluromethyl), cyano, or the like.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, fluoroalkyl (such as trifluromethyl), cyano, or the like.

The term "carbocycle" is art recognized and includes an aromatic or non-aromatic ring in which each atom of the ring is carbon. The flowing art-recognized terms have the following meanings: "nitro" means —NO$_2$; the term "halogen" designates —F, —Cl, —Br or —I; the term "sulfhydryl" means —SH; the term "hydroxyl" means —OH; and the term "sulfonyl" means —SO$_2^-$.

The terms "amine" and "amino" are art-recognized and include both unsubstituted and substituted amines, e.g., a moiety that may be represented by the general formulas:

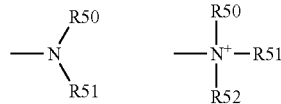

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and includes a moiety that may be represented by the general formula:

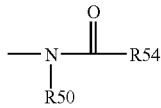

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

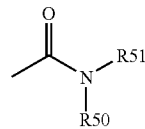

wherein R50 and R51 are as defined above. Certain embodiments of the amide in the present invention will not include amides which may be unstable.

The term "alkylthio" is art recognized and includes an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethylthio, and the like.

The term "carbonyl" is art recognized and includes such moieties as may be represented by the general formulas:

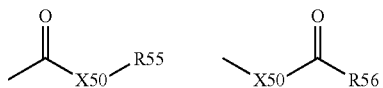

wherein X50 is a bond or represents an oxygen or a sulfur, and R55 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 is not hydrogen, the formula represents an "ester". Where X50 is an oxygen, and R55 is as first defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thioester." Where X50 is a sulfur and R55 is hydrogen, the formula represents a "thiocarboxylic acid." Where X50 is a sulfur and R56 is hydrogen, the formula represents a "thioformate." On the other hand, where X50 is a bond, and R55 is not hydrogen, the above formula represents a "ketone" group. Where X50 is a bond, and R55 is hydrogen, the above formula represents an "aldehyde" group.

The terms "oxime" and "oxime ether" are art-recognized and refer to moieties that may be represented by the general formula:

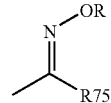

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and includes a moiety that may be represented by the general formula:

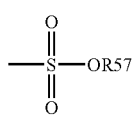

in which R57 is an electron pair, hydrogen, alkyl, cycloalkyl, or aryl.

The term "sulfate" is art recognized and includes a moiety that may be represented by the general formula:

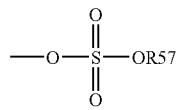

in which R57 is as defined above.

The term "sulfonamido" is art recognized and includes a moiety that may be represented by the general formula:

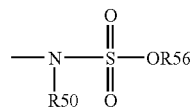

in which R50 and R56 are as defined above.

The term "sulfamoyl" is art-recognized and includes a moiety that may be represented by the general formula:

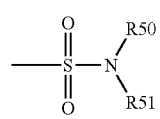

in which R50 and R51 are as defined above.

The term "sulfonyl" is art recognized and includes a moiety that may be represented by the general formula:

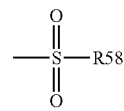

in which R58 is one of the following: hydrogen, alkyl, alkenyl, alkynyl, cycloalkyl, heterocyclyl, aryl or heteroaryl.

The term "sulfoxido" is art recognized and includes a moiety that may be represented by the general formula:

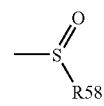

in which R58 is defined above.

The term "phosphoryl" is art-recognized and may in general be represented by the formula:

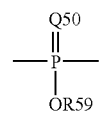

wherein Q50 represents S or O, and R59 represents hydrogen, a lower alkyl or an aryl. When used to substitute, e.g., an alkyl, the phosphoryl group of the phosphorylalkyl may be represented by the general formulas:

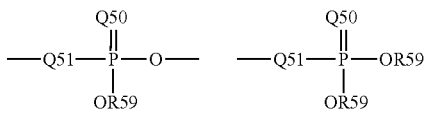

wherein Q50 and R59, each independently, are defined above, and Q51 represents O, S or N. When Q50 is S, the phosphoryl moiety is a "phosphorothioate".

The term "phosphoramidite" is art recognized and includes moieties represented by the general formulas:

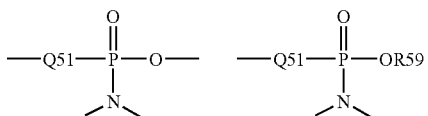

wherein Q51, R50, R51 and R59 are as defined above.

The term "phosphonamidite" is art recognized and includes moieties represented by the general formulas:

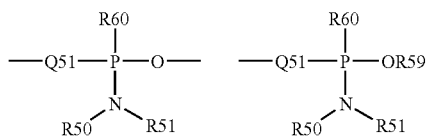

wherein Q51, R50, R51 and R59 are as defined above, and R60 represents a lower alkyl or an aryl.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, etc., when it occurs more than once in any structure, is intended to be independent of its definition elsewhere in the same structure unless otherwise indicated expressly or by the context.

For purposes of the invention, the chemical elements are identified in accordance with the Periodic Table of the Elements, CAS version, Handbook of Chemistry and Physics, 67th Ed., 1986-87, inside cover.

Overview. In certain embodiments, ionic liquids of the instant invention may be represented by the formula $[X_xBY_{4-n}]^{+(n-1)}(n-1)Z^{-1}$, wherein X refers to a Lewis base, Y refers to a substituent covalently bonded to boron, $Z^{-1}$ is a charge diffuse anion, and x is 2, 3 or 4. In certain embodiments, the ionic liquids of the instant invention are of the general type $[X_2BY_2]^{+1}Tf_2N^{-1}$ wherein each X is a either a tertiary amine or a N-alkylimidazole.

Related boronium ions of the type $[(N-alkylimidazole)_2BH_2]^{+1}$ have been reported as iodide salts (NMR characterization) and directly used as presursors of monoanionic chelating bis(carbene) ligands; and similarly, a bis(N—H-imidazole) boronium ion was reported as an intermediate in the synthesis of a series of macrocyclic imidazolyl boranes. R. Frankel, J. Kniczek, W. Ponikwar, H. Noth, K. Polborn and W. P. Fehlhammer *Inorg. Chim. Acta* 2001, 312, 23; and A. Weiss, V. Barba, H. Pritzkow and W. Siebert *J. Organomet. Chem.* 2003, 680, 294.

While a handful of boronium salts with melting points nominally less than about 100° C. have been reported, only one (a hygroscopic iodide salt of non-analytical purity) being liquid at, near or below room temperature and this most likely was due to hydratation and not true ionic liquid character. In addition, excepting the latter, all are $PF_6^-$ salts that were prepared expressly in order to more easily isolate crystalline materials. N. E. Miller and E. L. Muetterties *J. Am. Chem. Soc.* 1964, 86, 1033; J. E. Douglass, J. D. Fellman, R. Carpenter, H.-M. Shih and Y.-F. Chiang *J. Org. Chem.* 1969, 34, 3666; M. L. Denniston, M. Chiusano, J. Brown and D. R. Martin *J. Inorg. Nucl. Chem.* 1976, 38, 379. It is also noted that $PF_6$— has fallen into disfavor for IL formulation due to its hydrolytic instability. R. P. Swatloski, J. D. Holbrey and R. D. Rogers *Green Chem.* 2003, 5, 361.

Table I (below) shows several examples of novel [(N-alkylimidazole)(amine)$BH_2$]$^{+1}$$Tf_2N^{-1}$ ("boronium-based") ionic liquids. The generalized structure of each bears a striking similarity to N,N'-dialkylimidazolium ions, the latter being key cations for ionic liquid formulation. The —$H_2$B—$NR_3$ groups of the boronium ions are isoelectronic and isostructural with —$H_2$C—$CR_3$ N-alkyl counterparts, and are in many ways easier to prepare. Significantly, all manifest the highly valued property of hydrophobicity and most are mobile room-temperature liquids. Compound 1 is the only one of these IL which is not a room-temperature liquid; the DSC of 1 (10° C. per minute) of crystalline 1 gave a sharp mp at 60.2° C.

TABLE 1

[(N-alkyl-imidazole)(amine)BH$_2$]$^{+1}$ Tf$_2$N$^{-1}$ Ionic Liquids

| Compound | Imidazole | Tertiary amine | C$^2$—H δ* |
|---|---|---|---|
| 1 | 1-methyl | trimethyl | 8.14 |
| 2 | 1-methyl | triethyl | 8.14 |
| 3 | 1-methyl | di(n-butyl)methyl | 8.21 |
| 4 | 1-butyl | trimethyl | 8.28 |
| 5 | 1-butyl | triethyl | 8.21 |
| 6 | 1-butyl | quinuclidine | 8.20 |
| 7 | 1,2-dimethyl | trimethyl | n/a |
| 8 | 1-decyl-2-methyl | trimethyl | n/a |

*imidazolium ring C$^2$—H proton, 300 mHz, 0.5 M acetone-d$^6$

Structure of Boroniums. In order to confirm the general structures of the boronium cations of Table 1, we undertook a single-crystal X-ray study of 1 (FIG. 1), the simplest of the salts. The asymmetric unit in the crystal consists of a fully ordered cation and two independent halves of anions disordered about centers of inversion. Though resolved, the anion disorder is extensive and indicative of very weak interactions between the cation H-atoms and the anion.

The overall structure and packing are not remarkable. An analysis of the bond distances and angles within the imidazolium ring reveals little effect from the boronium substituent. The ring parameters are quite similar to previously reported dialkyl-substituted imidazolium cations. J. J. Golding, D. R. Macfarlane, L. Spiccia, M. Forsyth, B. W. Skelton and A. H. White *Chem. Commun.* 1998, 1593; J. Fuller, R. T. Carlin, H. C. DeLong, D. Haworth *Chem. Commun.* 1994, 299; and J. D. Holbrey, W. M. Reichert, M. Nieuwenhuyzen, O. Sheppard, C. Hardacre and R. D. Rogers *Chem. Commun.* 2003, 476. The anion is in the more common, low energy trans conformation, which is similar to that observed in [(C$_2$)$_3$im][NTf$_2$]. J. D. Holbrey, W. M. Reichert and R. D. Rogers *Dalton Trans.* 2004, 2267. A comparison of all intermolecular contacts less than van der Waals reveals very few and very weak interactions between the cations and anions, similar to those observed in [C$_1$ mim][NTf$_2$], [(C$_2$)$_3$im][NTf$_2$], and [C$_2$C$_1$benzylim] [NTf$_2$]. The closest ring-H contact is 2.382 Å from the C$^2$—H atom to one disordered oxygen position of one of the independent anions. There is also a contact between the C$^2$—H and the nitrogen of the same anion at a distance of 2.52 Å. As observed previously with [imidazolium]$^+$Tf$_2$N$^-$ salts, there are no strong hydrogen bonds to direct the packing in the crystal lattice.

Synthesis. The syntheses of the imidazole-boronium cations are accomplished using careful modifications of earlier protocols. J. M. Garrett and G. E. Ryschkewitsch, *Inorganic Syntheses*, ed. R. W. Parry, McGraw-Hill, New York, 1970, vol. 12, p. 132. Conceptually, all are based on the modular assembly of commercially available units, e.g. a tertiary amine, an N-heterocycle and a source of BH$_2$$^+$ (commonly an amine-borane complex). N. E. Miller and E. L. Muetterties *J. Am. Chem. Soc.* 1964, 86, 1033; J. E. Douglass, J. D. Fellman, R. Carpenter, H.-M. Shih and Y.-F. Chiang *J. Org. Chem.* 1969, 34, 3666; and M. L. Denniston, M. Chiusano, J. Brown and D. R. Martin *J. Inorg. Nucl. Chem.* 1976, 38, 379.

In all cases, isolation of precursor iodide salts is followed by anion metathesis in water using LiTf$_2$N; the final products separate as hydrophobic phases. While conventional imidazolium IL are often initially isolated as highly colored materials, the boronium r and Tf$_2$N salts are completely colorless, conceivably the result of a difference in susceptibility on the part of the boronium ions towards interionic charge-transfer. C. M. Gordon, in *Ionic Liquids in Synthesis*; P. Wasserscheid and T. Welton, Eds.; Wiley-VCH: Weinheim, 2003; pp 17-19; C. Hilgers and P. Wasserscheid, ibid; pp 21-24; T. M. Bockman and J. K. Kochi *J. Am. Chem. Soc.* 1989, 111, 4669; S. Pommeret, J.-C. Mialocq, B. Tokarczyk and W. Jarzeba *Res. Chem. Intermed.* 2001, 27 (7-8), 795.

A different approach to the formation of the ionic liquids of the invention is the use of hydroboration of alkenes. An example of the synthesis of a salt of the invention with boron-carbon bonds is shown in Scheme 1 below.

Scheme 1. One approach to the synthesis of boronium IL salts with carbon-boron bonds.

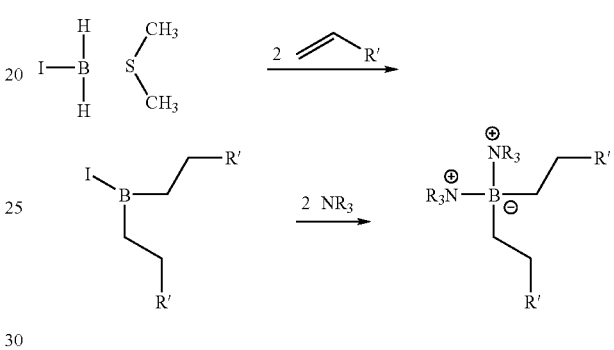

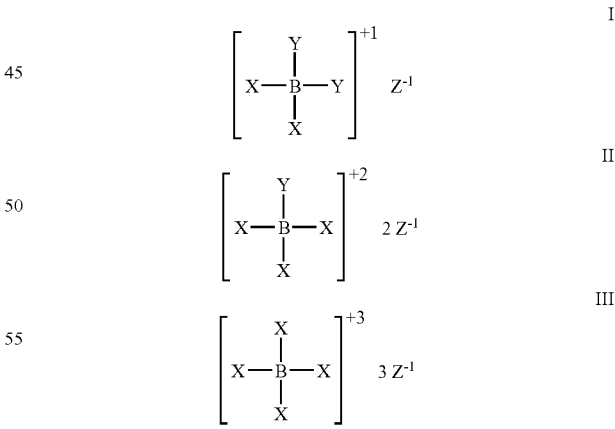

Characteristics and Uses of Ionic Liquids of the Present Inventions. The purity of ionic liquids produced by the processes of this inventions can often be greater than 50%, preferably greater than 60%, more preferably greater than 70%, most preferably greater than 80%. This is often advantageous for processes that require high purity materials such as in the electronics industry.

Compounds of the Invention. Another aspect of the present invention relates to a salt represented by formula I, II, or III:

$$\begin{bmatrix} & Y & \\ X - & B & - Y \\ & X & \end{bmatrix}^{+1} Z^{-1} \quad \text{I}$$

$$\begin{bmatrix} & Y & \\ X - & B & - X \\ & X & \end{bmatrix}^{+2} 2\,Z^{-1} \quad \text{II}$$

$$\begin{bmatrix} & X & \\ X - & B & - X \\ & X & \end{bmatrix}^{+3} 3\,Z^{-1} \quad \text{III}$$

wherein, independently for each occurrence,

X is —NR$^A$(R$^B$)$_2$ or an optionally substituted heterocycle selected from the consisting of pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium and diazepinium;

Y is hydrogen, halogen, alkyl, fluoroalkyl, cycloalkyl, heterocycloalkyl, cycloalkenyl, heterocycloalkenyl, aryl, heteroaryl, $-OR^C$, $-N(R^C)_2$, $-SR^C$, $-C(=O)OR^C$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-S(=O)_2OR^C$, $-C(=O)R^C$, $-C(=NR^C)R^C$, $-C(=S)R^C$, $-C(R^C)=C(R^C)_2$, $-C\equiv CR^C$ or $-[C(R^C)_2]_p-R^D$;

$Z^{-1}$ is a halide or a charge-diffuse anion;

$R^A$ is hydrogen, alkyl, fluoroalkyl, cycloalkyl, aryl, heteroaryl, aralkyl, heteroaralkyl or $-[C(R^C)_2]_p-R^D$;

$R^B$ is alkyl, fluoroalkyl, cycloalkyl, aryl, heteroaryl, aralkyl, heteroaralkyl or $-[C(R^C)_2]_p-R^D$;

$R^C$ is hydrogen, halogen, alkyl, fluoroalkyl, cycloalkyl, heterocycloalkyl, alkenyl, cycloalkenyl, heterocycloalkenyl, alkynyl, aryl, heteroaryl, aralkyl or heteroaralkyl;

$R^D$ is hydrogen, halogen, alkyl, fluoroalkyl, cycloalkyl, heterocycloalkyl, cycloalkenyl, heterocycloalkenyl, aryl, heteroaryl, $-OR^C$, $-N(R^C)_2$, $-SR^C$, $-C(=O)OR^C$, $-C(=O)N(R^C)_2$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-S(=O)_2OR^C$, $-C(=O)R^C$, $-C(=NR^C)R^C$, $-C(=S)R^C$, $-C(R^C)=C(R^C)_2$, $-C\equiv CR^C$ or $-[C(R^C)_2]_p-R^C$;

p is 1-10 inclusive;

optionally, in formula I, the two instances of Y, taken together with the boron to which they are bound, form an optionally substituted 5-, 6-, 7- or 8-membered ring;

optionally two instance of X, taken with the boron to which they are bound, form an optionally substituted 5-, 6-, 7- or 8-membered ring;

optionally one instance of X and one instance of Y, taken together with the boron to which they are bound, form an optionally substituted 5-, 6-, 7- or 8-membered ring;

optionally two instances of $R^B$, taken together with the nitrogen to which they are bound, form an optionally substituted 5-, 6-, 7- or 8-membered ring; and optionally $R^A$ and two instances of $R^B$, taken together with the nitrogen to which they are bound, for an optionally substituted 5-, 6-, 7-, 8-membered bicyclo-ring;

provided that the salt of formula I, II, or III has a melting point less than or equal to about 100° C.

In certain embodiments, the present invention relates to the aforementioned salt, wherein at least one of said optionally substituted heterocycles is bonded to boron through a heteroatom.

In certain embodiments, the present invention relates to the aforementioned salt, wherein X is $-NR^A(R^B)_2$ or an optionally substituted heterocycle selected from the consisting of imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium and diazepinium.

In certain embodiments, the present invention relates to the aforementioned salt, wherein said optionally substituted heterocycle is optionally substituted with one or more substituents selected from the group consisting of halogen, alkyl, fluoroalkyl, cycloalkyl, heterocycloalkyl, cycloalkenyl, heterocycloalkenyl, aryl, heteroaryl, $-OR^C$, $-N(R^C)_2$, $-SR^C$, $-C(=O)OR^C$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-S(=O)_2OR^C$, $-C(=O)R^C$, $-C(=NR^C)R^C$, $-C(=S)R^C$, $-C(R^C)=C(R^C)_2$, $-C\equiv CR^C$ and $-[C(R^C)_2]_p-R^D$.

In certain embodiments, the present invention relates to the aforementioned salt, wherein said optionally substituted heterocycle is optionally substituted with one or more groups selected from the group consisting of alkyl and fluoroalkyl.

In certain embodiments, the present invention relates to the aforementioned salt, wherein Y is halogen, alkyl, fluoroalkyl, cycloalkyl, heterocycloalkyl, cycloalkenyl, heterocycloalkenyl, aryl, heteroaryl, $-OR^C$, $-NC)_2$, $-SR^C$, $-C(=O)OR^C$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-C(=O)R^C$, $-C(=NR^C)R^C$, $-C(=S)R^C$, $C(R^C)=C(R^C)_2$, $-C\equiv CR^C$ or $-[C(R^C)_2]_p-R^D$.

In certain embodiments, the present invention relates to the aforementioned salt, wherein Y is hydrogen, alkyl, fluoroalkyl, cycloalkyl, heterocycloalkyl, cycloalkenyl, heterocycloalkenyl, aryl, heteroaryl, $-OR^C$, $-N(R^C)_2$, $-SR^C$, $-C(=O)OR^C$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-C(=O)R^C$, $-C(=NR^C)R^C$, $-C(=S)R^C$, $-C(R^C)=C(R^C)_2$, $-C\equiv CR^C$ or $-[C(R^C)_2]_p-R^D$.

In certain embodiments, the present invention relates to the aforementioned salt, wherein Y is alkyl, fluoroalkyl, cycloalkyl, heterocycloalkyl, cycloalkenyl, heterocycloalkenyl, aryl, heteroaryl, $-OR^C$, $-N(R^C)_2$, $-SR^C$, $-C(=O)OR^C$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-C(=O)R^C$, $-C(=NR^C)R^C$, $-C(=S)R^C$, $C(R^C)=C(R^C)_2$, $-C\equiv CR^C$ or $-[C(R^C)_2]_p-R^D$, In certain embodiments, the present invention relates to the aforementioned salt, wherein $Z^{-1}$ represents halide, boron tetrafluoride, boron tetraphenyl, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide or bis(p-toluenesulfonyl)amide.

In certain embodiments, the present invention relates to the aforementioned salt, wherein $Z^{-1}$ represents bromide, iodide, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide or bis(p-toluenesulfonyl)amide.

In certain embodiments, the present invention relates to the aforementioned salt, wherein $Z^{-1}$ represents iodide, bis(methanesulfonyl)amide, bis(trifluoromethanesulfonyl)amide, bis(benzenesulfonyl)amide or bis(p-toluenesulfonyl)amide.

In certain embodiments, the present invention relates to the aforementioned salt, wherein $Z^{-1}$ represents bis(trifluoromethanesulfonyl)amide or (trifluoromethanesulfonyl)(trifluoroacetyl)amide.

In certain embodiments, the present invention relates to the aforementioned salt, provided that the salt of formula I, II, or III has a melting point less than or equal to about 45° C.

In certain embodiments, the present invention relates to the aforementioned salt, provided that the salt of formula I, II, or III has a melting point less than or equal to about 25° C.

Another aspect of the present invention relates to a salt represented by formula IV, V, or VI:

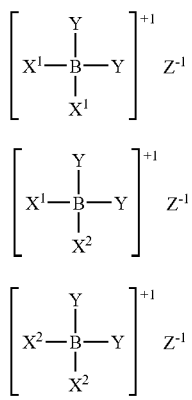

wherein, independently for each occurrence, $X^1$ is $NR^A(R^B)_2$;

$X^2$ is an optionally substituted heterocycle selected from the group consisting of pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium and diazepinium;

Y is hydrogen, halogen, alkyl, fluoroalkyl, cycloalkyl, heterocycloalkyl, cycloalkenyl, heterocycloalkenyl, aryl, heteroaryl, —$OR^C$, —$N(R^C)_2$, —$SR^C$, —$C(=O)OR^C$, —OC(=O)$R^C$, —$NR^CC(=O)R^C$, —$C(=O)N(R^C)_2$, —$C(=O)SR^C$, —$SC(=O)R^C$, —$S(=O)R^C$, —$S(=O)_2R^C$, —$S(=O)_2OR^C$, —$C(=O)R^C$, —$C(=NR^C)R^C$, —$C(=S)R^C$, —$C(R^C)=C(R^C)_2$, —$C\equiv CR^C$ or —$[C(R^C)_2]_p$—$R^D$;

$Z^{-1}$ is halide, boron tetrafluoride, boron tetraphenyl, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide or bis(p-toluenesulfonyl)amide;

$R^A$ is hydrogen, alkyl, fluoroalkyl, cycloalkyl, aryl, heteroaryl, aralkyl, heteroaralkyl or —$[C(R^C)_2]_p$—$R^D$;

$R^B$ is alkyl, fluoroalkyl, cycloalkyl, aryl, heteroaryl, aralkyl, heteroaralkyl or —$[C(R^C)_2]_p$—$R^D$;

$R^C$ is hydrogen, halogen, alkyl, fluoroalkyl, cycloalkyl, heterocycloalkyl, alkenyl, cycloalkenyl, heterocycloalkenyl, alkynyl, aryl, heteroaryl, aralkyl, or heteroaralkyl;

$R^D$ is hydrogen, halogen, alkyl, fluoroalkyl, cycloalkyl, heterocycloalkyl, cycloalkenyl, heterocycloalkenyl, aryl, heteroaryl, —$OR^C$, —$N(R^C)_2$, —$SR^C$, —$C(=O)OR^C$, —$C(=O)N(R^C)_2$, —$OC(=O)R^C$, —$NR^CC(=O)R^C$, —$C(=O)N(R^C)_2$, —$C(=O)SR^C$, —$SC(=O)R^C$, —$S(=O)R^C$, —$S(=O)_2R^C$, —$S(=O)_2OR^C$, —$C(=O)R^C$, —$C(=NR^C)R^C$, —$C(=S)R^C$, —$C(R^C)=C(R^C)_2$, —$C\equiv CR^C$ or $[C(R^C)_2]_p$—$R^C$;

p is 1-10 inclusive;

optionally two $X^1$, two $X^2$, two Y, an $X^1$ and a Y, an $X^2$ and a Y, and a $X^1$ and an $X^2$, taken together with the boron to which they are bound, form an optionally substituted 5-, 6-, 7- or 8-membered ring;

optionally two instances of $R^B$, taken together with the nitrogen to which they are bound, form an optionally substituted 5-, 6-, 7- or 8-membered ring; and optionally $R^A$ and two instances of $R^B$, taken together with the nitrogen to which they are bound, for an optionally substituted 5-, 6-, 7-, 8-membered bicyclo-ring;

provided that the salt of formula VI, V, or VI has a melting point less than or equal to about 100° C.

In certain embodiments, the present invention relates to the aforementioned salt, wherein at least one of said optionally substituted heterocycles is bonded to boron through a heteroatom.

In certain embodiments, the present invention relates to the aforementioned salt, wherein X is —$NR^A(R^B)_2$ or an optionally substituted heterocycle selected from the consisting of imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium and diazepinium.

In certain embodiments, the present invention relates to the aforementioned salt, wherein said optionally substituted heterocycle is optionally substituted with one or more substituents selected from the group consisting of halogen, alkyl, fluoroalkyl, cycloalkyl, heterocycloalkyl, cycloalkenyl, heterocycloalkenyl, aryl, heteroaryl, —$OR^C$, —$N(R^C)_2$, —$SR^C$, —$C(=O)OR^C$, —$OC(=O)R^C$, —$NR^CC(=O)R^C$, —$C(=O)N(R^C)_2$, —$C(=O)SR^C$, —$SC(=O)R^C$, —$S(=O)R^C$, —$S(=O)R^C$, —$S(=O)_2R^C$, —$S(=O)_2OR^C$, —$C(=O)R^C$, —$C(=NR^C)R^C$, —$C(=S)R^C$, —$C(R^C)=C(R^C)_2$, —$C\equiv CR^C$ and —$[C(R^C)_2]_p$—$R^D$.

In certain embodiments, the present invention relates to the aforementioned salt, wherein said optionally substituted heterocycle is optionally substituted with one or more groups selected from the group consisting of alkyl and fluoroalkyl.

In certain embodiments, the present invention relates to the aforementioned salt, wherein Y is halogen, alkyl, fluoroalkyl, cycloalkyl, heterocycloalkyl, cycloalkenyl, heterocycloalkenyl, aryl, heteroaryl, —$OR^C$, —$N(R^C)_2$, —$SR^C$, —$C(=O)OR^C$, —$OC(=O)R^C$, —$NR^CC(=O)R^C$, —$C(=O)N(R^C)_2$, —$C(=O)SR^C$, —$SC(=O)R^C$, —$S(=O)R^C$, —$S(=O)_2R^C$, —$C(=O)R^C$, —$C(=NR^C)R^C$, —$C(=S)R^C$, $C(R^C)=C(R^C)_2$, —$C\equiv CR^C$ or —$[C(R^C)_2]_p$—$R^D$.

In certain embodiments, the present invention relates to the aforementioned salt, wherein Y is hydrogen, alkyl, fluoroalkyl, cycloalkyl, heterocycloalkyl, cycloalkenyl, heterocycloalkenyl, aryl, heteroaryl, —$OR^C$, —$N(R^C)_2$, —$SR^C$, —$C(=O)OR^C$, —$OC(=O)R^C$, —$NR^CC(=O)R^C$, —$C(=O)N(R^C)_2$, —$C(=O)SR^C$, —$SC(=O)R^C$, —$S(=O)R^C$, —$S(=O)_2R^C$, —$C(=O)R^C$, —$C(=NR^C)R^C$, —$C(=S)R^C$, —$C(R^C)=C(R^C)_2$, —$C\equiv CR^C$ or —$[C(R^C)_2]_p$—$R^D$.

In certain embodiments, the present invention relates to the aforementioned salt, wherein Y is alkyl, fluoroalkyl, cycloalkyl, heterocycloalkyl, cycloalkenyl, heterocycloalkenyl, aryl, heteroaryl, —$OR^C$, —$N(R^C)_2$, —$SR^C$, —$C(=O)OR^C$, —$OC(=O)R^C$, —$NR^CC(=O)R^C$, —$C(=O)N(R^C)_2$, —$C(=O)SR^C$, —$SC(=O)R^C$, —$S(=O)R^C$, —$S(=O)_2R^C$, —$C(=O)R^C$, —$C(=NR^C)R^C$, —$C(=S)R^C$, —$C(R^C)=C(R^C)_2$, —$C\equiv CR^C$ or —$[C(R^C)_2]_p$—$R^D$.

In certain embodiments, the present invention relates to the aforementioned salt, wherein Y is hydrogen, halogen, alkyl, fluoroalkyl, cycloalkyl, heterocycloalkyl, cycloalkenyl, heterocycloalkenyl, aryl, heteroaryl or —$[C(R^C)_2]_p$—$R^D$.

In certain embodiments, the present invention relates to the aforementioned salt, wherein Y is halogen, alkyl, fluoroalkyl, cycloalkyl, heterocycloalkyl, cycloalkenyl, heterocycloalkenyl, aryl, heteroaryl or —$[C(R^C)_2]_p$—$R^D$.

In certain embodiments, the present invention relates to the aforementioned salt, wherein Y is hydrogen, alkyl, fluoroalkyl, cycloalkyl, heterocycloalkyl, cycloalkenyl, heterocycloalkenyl, aryl, heteroaryl or $-[C(R^C)_2]_p-R^D$.

In certain embodiments, the present invention relates to the aforementioned salt, wherein Y is alkyl, fluoroalkyl, cycloalkyl, heterocycloalkyl, cycloalkenyl, heterocycloalkenyl, aryl, heteroaryl or $-[C(R^C)_2]_p-R^D$.

In certain embodiments, the present invention relates to the aforementioned salt, wherein Y is alkyl or $-[C(H)_2]_2-R^D$.

In certain embodiments, the present invention relates to the aforementioned salt, wherein $R^A$ is alkyl, fluoroalkyl, cycloalkyl, aryl, heteroaryl, aralkyl, heteroaralkyl or $-[C(R^C)_2]_p-R^D$.

In certain embodiments, the present invention relates to the aforementioned salt, wherein $R^A$ is alkyl.

In certain embodiments, the present invention relates to the aforementioned salt, wherein $R^B$ is alkyl.

In certain embodiments, the present invention relates to the aforementioned salt, wherein $R^A$ is alkyl; and $R^B$ is alkyl.

In certain embodiments, the present invention relates to the aforementioned salt, wherein $Z^{-1}$ represents bromide, iodide, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide or bis(p-toluenesulfonyl)amide.

In certain embodiments, the present invention relates to the aforementioned salt, wherein $Z^{-1}$ represents iodide, bis(methanesulfonyl)amide, bis(trifluoromethanesulfonyl)amide, bis(benzenesulfonyl)amide or bis(p-toluenesulfonyl)amide.

In certain embodiments, the present invention relates to the aforementioned salt, wherein $Z^{-1}$ represents bis(trifluoromethanesulfonyl)amide or (trifluoromethanesulfonyl)(trifluoroacetyl)amide.

In certain embodiments, the present invention relates to the aforementioned salt, provided that the salt of formula VI, V, or VI has a melting point less than or equal to about 45° C.

In certain embodiments, the present invention relates to the aforementioned salt, provided that the salt of formula VI, V, or VI has a melting point less than or equal to about 25° C.

Another aspect of the present invention relates to a salt represented by formula VII or VIII:

$$\left[\begin{array}{c} R^5 \\ Y \\ X^1-B-N \\ Y \\ R^2 \end{array} \begin{array}{c} R^4 \\ \\ N \\ R^3 \end{array}\right]^{+1} Z^{-1} \quad \text{VII}$$

$$\left[\begin{array}{c} R^2 \\ Y \\ X^1-B-N \\ Y \\ R^2 \end{array} \begin{array}{c} R^4 \\ \\ R^5 \\ R^4 \end{array}\right]^{+1} Z^{-1} \quad \text{VIII}$$

wherein, independently for each occurrence, $X^1$ is $-NR^A(R^B)_2$; or an optionally substituted heterocycle selected from the group consisting of pyridinium and imidazolium;

Y is hydrogen, halogen, alkyl, fluoroalkyl, cycloalkyl, heterocycloalkyl, cycloalkenyl, heterocycloalkenyl, aryl, heteroaryl, $-OR^C$, $-N(R^C)_2$, $-SR^C$, $-C(=O)OR^C$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-S(=O)_2OR^C$, $C(=O)R^C$, $-C(=NR^C)R^C$, $-C(=S)R^C$, $-C(R^C)=C(R^C)_2$, $-C\equiv CR^C$ or $-[C(R^C)_2]_p-R^D$;

$Z^{-1}$ is halide, boron tetrafluoride, boron tetraphenyl, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide or bis(p-toluenesulfonyl)amide;

$R^A$ is hydrogen, alkyl, fluoroalkyl, cycloalkyl, aryl, heteroaryl, aralkyl, heteroaralkyl or $[C(R^C)_2]_p-R^D$;

$R^B$ is alkyl, fluoroalkyl, cycloalkyl, aryl, heteroaryl, aralkyl, heteroaralkyl or $[C(R^C)_2]_p-R^D$;

$R^C$ is hydrogen, halogen, alkyl, fluoroalkyl, cycloalkyl, heterocycloalkyl, alkenyl, cycloalkenyl, heterocycloalkenyl, alkynyl, aryl, heteroaryl, aralkyl or heteroaralkyl;

$R^D$ is hydrogen, alkyl, fluoroalkyl, cycloalkyl, heterocycloalkyl, cycloalkenyl, heterocycloalkenyl, aryl, heteroaryl, $-OR^C$, $-N(R^C)_2$, $-SR^C$, $C(=O)OR^C$, $-C(=O)N(R^C)_2$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-S(O)_2R^C$, $-C(=O)R^C$, $-C(=NR^C)R^C$, $-C(=S)R^C$, $-C(R^C)=C(R^C)_2$, $-C\equiv CR^C$ or $-[C(R^C)_2]_p-R^C$;

$R^2$ is hydrogen, halogen, alkyl, fluoroalkyl, cycloalkyl, heterocycloalkyl, cycloalkenyl, heterocycloalkenyl, aryl, heteroaryl, $-OR^C$, $-N(R^C)_2$, $-SR^C$, $-C(=O)OR^C$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-S(=O)_2OR^C$, $-C(=O)R^C$, $-C(=NR^C)R^C$, $-C(=S)R^C$, $-C(R^C)=C(R^C)_2$, $-C\equiv CR^C$ or $-[C(R^C)_2]_p-R^D$;

$R^3$ is hydrogen, alkyl, fluoroalkyl, cycloalkyl, aryl, heteroaryl, aralkyl, heteroaralkyl or $-[C(R^C)_2]_p-R^D$;

$R^4$ is hydrogen, halogen, alkyl, fluoroalkyl, cycloalkyl, heterocycloalkyl, cycloalkenyl, heterocycloalkenyl, aryl, heteroaryl, $-OR^C$, $-N(R^C)_2$, $-SR^C$, $-C(=O)OR^C$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-S(=O)_2OR^C$, $-C(=O)R^C$, $-C(=NR^C)R^C$, $-C(=S)R^C$, $-C(R^C)=C(R^C)_2$, $-C\equiv CR^C$ or $-[C(R^C)_2]_p-R^D$;

$R^5$ is hydrogen, halogen, alkyl, fluoroalkyl, cycloalkyl, heterocycloalkyl, cycloalkenyl, heterocycloalkenyl, aryl, heteroaryl, $-OR^C$, $-N(R^C)_2$, $-SR^C$, $-C(=O)OR^C$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-S(=O)_2OR^C$, $-C(=O)R^C$, $-C(=NR^C)R^C$, $-C(=S)R^C$, $-C(R^C)=C(R^C)_2$, $-C\equiv CR^C$ or $-[C(R^C)_2]_p-R^D$;

optionally two instances of $R^B$, taken together with the nitrogen to which they are bound, form an optionally substituted 5-, 6-, 7- or 8-membered ring; and optionally $R^A$ and two instances of $R^B$, taken together with the nitrogen to which they are bound, for an optionally substituted 5-, 6-, 7-, 8-membered bicyclo-ring; and p is 1-10 inclusive;

provided that the salt of formula VII or VIII has a melting point less than or equal to about 100° C.

In certain embodiments, the present invention relates to the aforementioned salt, wherein Y is halogen, alkyl, fluoroalkyl, cycloalkyl, heterocycloalkyl, cycloalkenyl, heterocycloalkenyl, aryl, heteroaryl, $-OR^C$, $-N(R^C)_2$, $-SR^C$, $-C(=O)OR^C$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-C(=O)R^C$, $-C(=NR^C)R^C$, $-C(=S)R^C$, $-C(R^C)=C(R^C)_2$, $-C\equiv CR^C$ or $-[C(R^C)_2]_p-R^D$.

In certain embodiments, the present invention relates to the aforementioned salt, wherein Y is hydrogen, alkyl, fluoroalkyl, cycloalkyl, heterocycloalkyl, cycloalkenyl, heterocycloalkenyl, aryl, heteroaryl, $-OR^C$, $-N(R^C)_2$, $-SR^C$, $-C(=O)OR^C$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-C(=O)R^C$, $-C(=NR^C)R^C$, $-C(=S)R^C$, $-C(R^C)=C(R^C)_2$, $-C\equiv CR^C$ or $-[C(R^C)_2]_p-R^D$.

In certain embodiments, the present invention relates to the aforementioned salt, wherein Y is alkyl, fluoroalkyl, cycloalkyl, heterocycloalkyl, cycloalkenyl, heterocycloalkenyl, aryl, heteroaryl, $-OR^C$, $-N(R^C)_2$, $-SR^C$, $-C(=O)OR^C$, $-OC(=O)R^C$, $-NR^CC(=O)R^C$, $-C(=O)N(R^C)_2$, $-C(=O)SR^C$, $-SC(=O)R^C$, $-S(=O)R^C$, $-S(=O)_2R^C$, $-C(=O)R^C$, $-C(=NR^C)R^C$, $-C(=S)R^C$, $-C(R^C)=C(R^C)_2$, $-C\equiv CR^C$ or $-[C(R^C)_2]_p-R^D$.

In certain embodiments, the present invention relates to the aforementioned salt, wherein Y is hydrogen, halogen, alkyl, fluoroalkyl, cycloalkyl, heterocycloalkyl, cycloalkenyl, heterocycloalkenyl, aryl, heteroaryl or $-[C(R^C)_2]_p-R^D$.

In certain embodiments, the present invention relates to the aforementioned salt, wherein Y is halogen, alkyl, fluoroalkyl, cycloalkyl, heterocycloalkyl, cycloalkenyl, heterocycloalkenyl, aryl, heteroaryl or $-[C(R^C)_2]_p-R^D$.

In certain embodiments, the present invention relates to the aforementioned salt, wherein Y is hydrogen, alkyl, fluoroalkyl, cycloalkyl, heterocycloalkyl, cycloalkenyl, heterocycloalkenyl, aryl, heteroaryl or $-[C(R^C)_2]_p-R^D$.

In certain embodiments, the present invention relates to the aforementioned salt, wherein Y is alkyl, fluoroalkyl, cycloalkyl, heterocycloalkyl, cycloalkenyl, heterocycloalkenyl, aryl, heteroaryl or $-[C(R^C)_2]_p-R^D$.

In certain embodiments, the present invention relates to the aforementioned salt, wherein Y is alkyl or $-[C(H)_2]_2-R^D$.

In certain embodiments, the present invention relates to the aforementioned salt, wherein $R^A$ is alkyl, fluoroalkyl, cycloalkyl, aryl, heteroaryl, aralkyl, heteroaralkyl or $-[C(R^C)_2]_p-R^D$.

In certain embodiments, the present invention relates to the aforementioned salt, wherein $R^A$ is alkyl.

In certain embodiments, the present invention relates to the aforementioned salt, wherein $R^B$ is alkyl.

In certain embodiments, the present invention relates to the aforementioned salt, wherein $R^A$ is alkyl; and $R^B$ is alkyl.

In certain embodiments, the present invention relates to the aforementioned salt, wherein $R^2$ is hydrogen or alkyl.

In certain embodiments, the present invention relates to the aforementioned salt, wherein $R^3$ is alkyl.

In certain embodiments, the present invention relates to the aforementioned salt, wherein $R^4$ is hydrogen or alkyl.

In certain embodiments, the present invention relates to the aforementioned salt, wherein $R^5$ is hydrogen or alkyl.

In certain embodiments, the present invention relates to the aforementioned salt, wherein $R^2$ is hydrogen or alkyl; $R^3$ is alkyl; $R^4$ is hydrogen or alkyl; and $R^5$ is hydrogen or alkyl.

In certain embodiments, the present invention relates to the aforementioned salt, wherein $Z^{-1}$ represents bromide, iodide, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide or bis(p-toluenesulfonyl)amide.

In certain embodiments, the present invention relates to the aforementioned salt, wherein $Z^{-1}$ represents iodide, bis(methanesulfonyl)amide, bis(trifluoromethanesulfonyl)amide, bis(benzenesulfonyl)amide or bis(p-toluenesulfonyl)amide.

In certain embodiments, the present invention relates to the aforementioned salt, wherein $Z^{-1}$ represents bis(trifluoromethanesulfonyl)amide or (trifluoromethanesulfonyl)(trifluoroacetyl)amide.

In certain embodiments, the present invention relates to the aforementioned salt, provided that the salt of formula VII or VIII has a melting point less than or equal to about 45° C.

In certain embodiments, the present invention relates to the aforementioned salt, provided that the salt of formula VII or VIII has a melting point less than or equal to about 25° C.

Another aspect of the present invention relates to a salt selected from the group consisting of [(N-1-methylimidazole)(trimethylamine)BH$_2$]$^{+1}$Tf$_2$N$^{-1}$, [(N-1-methylimidazole)(triethylamine)BH$_2$]$^{+1}$Tf$_2$N$^{-1}$, [(N-1-methylimidazole)(di(n-butyl)methylamine)BH$_2$]$^{+1}$ Tf$_2$N$^{-1}$, [(N-1-butylimidazole)(trimethylamine)BH$_2$]$^{+1}$Tf$_2$N$^{-1}$, [(N-1-butylimidazole)(triethylamine)BH$_2$]$^{+1}$Tf$_2$N$^{-1}$, [(N-1-butylimidazole)(quinuclidine)BH$_2$]$^{+1}$Tf$_2$N$^{-1}$, [(N-1,2-dimethylimidazole)(trimethylamine)BH$_2$]$^{+1}$Tf$_2$N$^{-1}$ and [(N-1-decyl-2-methylimidazole)(trimethylamine)BH$_2$]$^{+1}$ Tf$_2$N$^{-1}$.

Ionic Liquids of the Invention as Organic Reaction Solvent. The new IL are capable of solubilizing a number of substrate types. Consequently, we conducted the Diels-Alder coupling of cyclopentadiene and methyl acrylate in 4 as a simple test of their use as solvents for organic reactions. The reaction proceeded cleanly, giving the expected bicyclic product in quantitative yield. The distribution of endo/exo isomers was 4.6, in accord with results previously reported for this reaction in other IL. For representative examples see: (a) A. Kumar and S. S. Pawar *J. Org. Chem.* 2004, 69, 1419; (b) A. Aggarwal, N. L. Lancaster, A. R. Sethi and T. Welton *Green Chem.* 2002, 4, 24; (c) M. J. Earle, P. B. McCormac and K. R. Seddon *Green Chem.,* 1999, 1, 23; and d) C. W. Lee *Tetrahedron Lett.* 1999, 40, 2461.

The similarity between 4 and conventional IL as Diels-Alder solvents notwithstanding, the boronium salts of the invention manifest a behavior sharply at odds with normal imidazolium cations. Despite several attempts to generate metal carbene complexes from these imidazolium ions using established approaches (W. A. Herrmann, T. Weskamp and V. P. W. Böhm, *Advances in Organometallic Chemistry*; R. West, Ed.; Academic Press: London, 2001; Vol. 48, p 1) involving Pd(OAc)$_2$ and rhodium alkoxide salts, we have been unable to isolate any such products. While β-linked carbenes may be made from boronium ions using n-BuLi, the apparent resistance of our ions towards carbene complex formation under less forcing conditions is potentially significant when making comparisons with conventional imidazolium IL.

Figure 2:
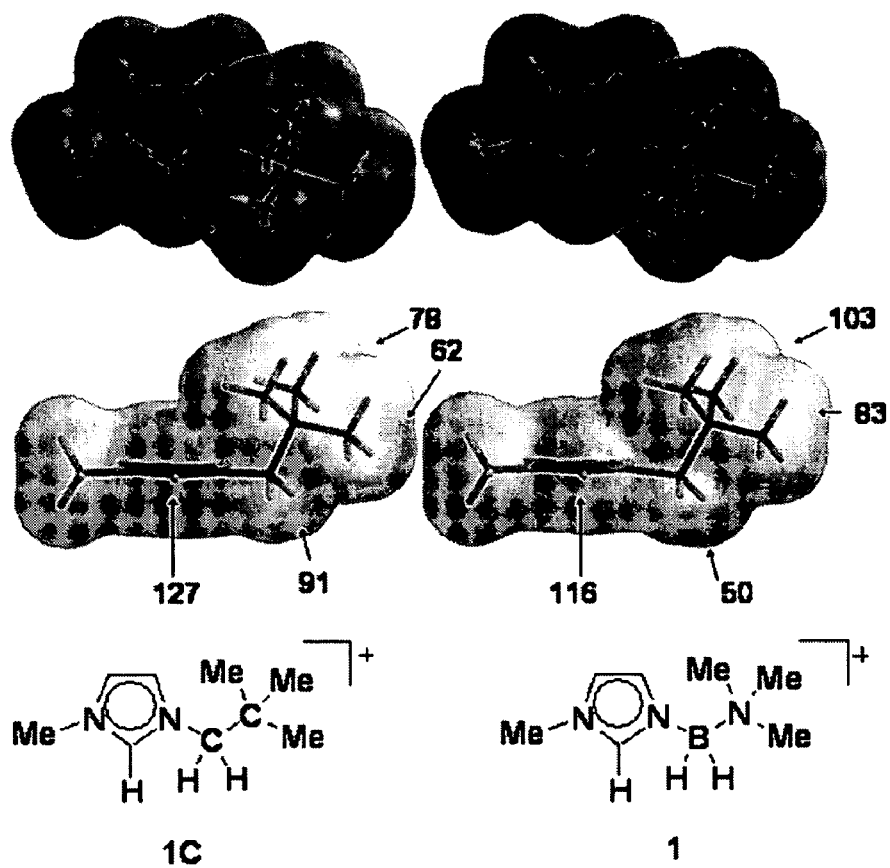
FIG. 2 depicts computed cation structures of ionic liquid [(N-1-methylimidazole) (trimethylamine)$BH_2]^{+1}Tf_2N^{-1}$ 1 (right) and its carbon analog 1C (left) showing select electropositive potentials.
Figure 3:
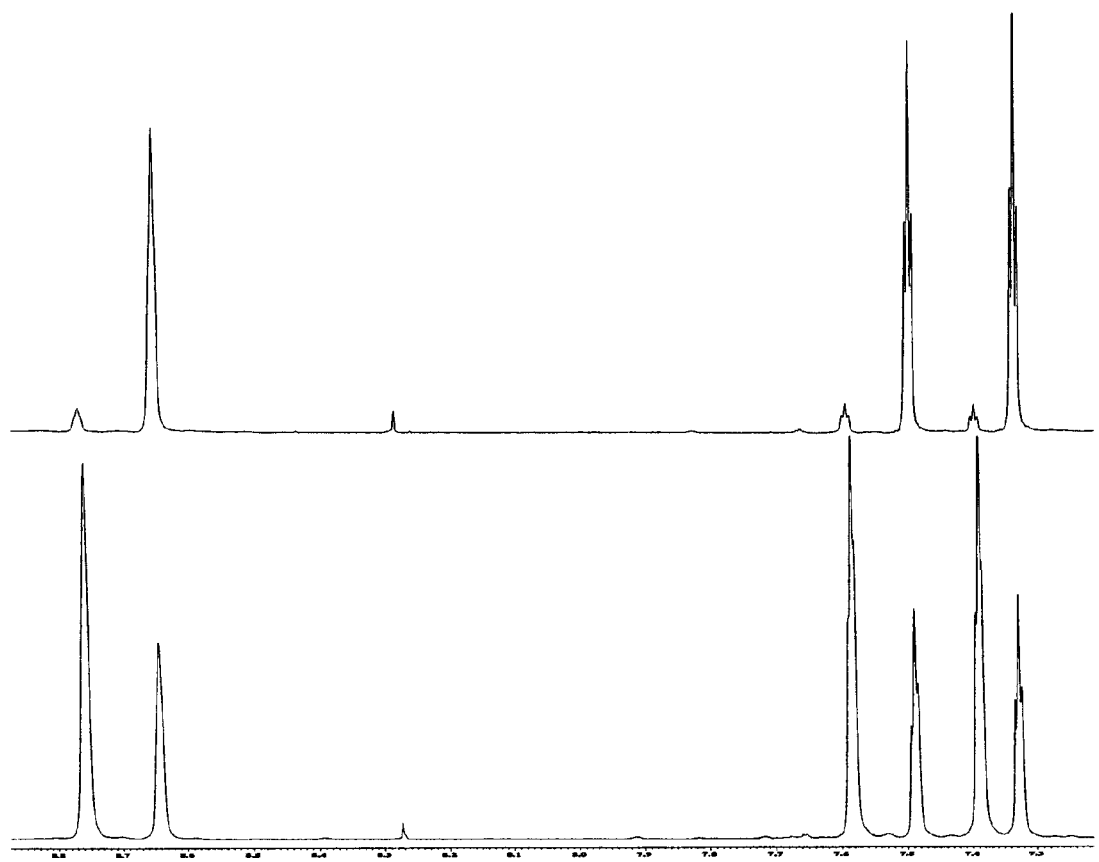
FIG. 3 depicts the $^1$H-NMR of the imidazole ring region of ionic liquid [(N-1-methylimidazole)(di(n-butyl)methylamine)$BH_2]^{+1}Tf_2N^{-1}$ 3 before (lower) and after (upper) overnight thermolysis in DMSO-$d_6$.
Figure 4:
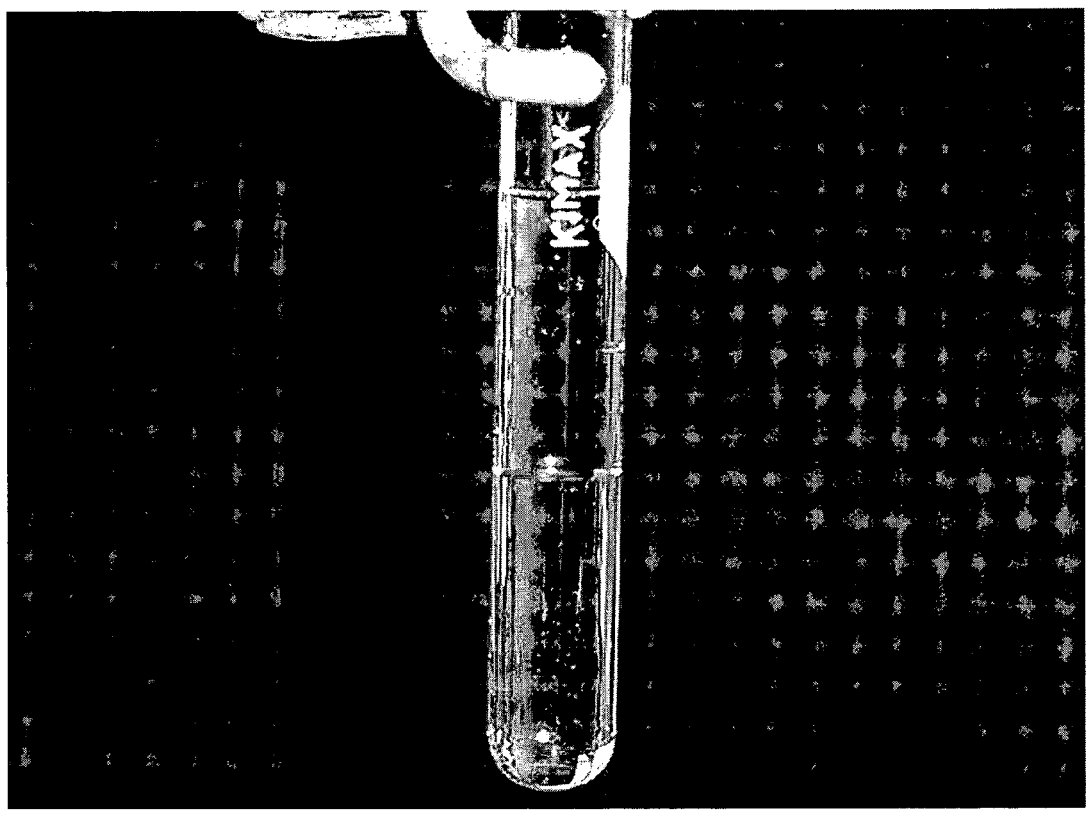
FIG. 4 depicts a photograph of a two-phase system composed of the boronium room temperature ionic liquid [(N-1-methylimidazole)(triethylamine)$BH_2]^{+1}Tf_2N^{-1}$ 1. The ionic liquid is the lower layer, water is the upper phase. Note both the hydrophobic character and the completely colorless nature of the room temperature ionic liquid.

Molecular Modeling. The simplicity with which the boronium ions are prepared and the structural diversity readily embodied in them each provide an important pragmatic basis for their use in formulating IL. Further, based upon an earlier computational study we anticipated that significant variations in electron density and charge distribution would be manifest in imidazole-boronium cations versus an N,N'-dialkylimidazolium norm. J. H. Davis, Jr. and J. D. Madura, *Tetrahedron Lett.* 1996, 37, 2729. In order to validate this premise, we performed high-level calculations on the cation of 1 as well as the putative isostructural conventional analog. Namely, DFT optimizations were carried out on an SGI Altix 350 supercomputer using the Gaussian03 suite of programs. The B3LYP density functional was chosen along with the 6-31 G(d,p) basis set. Optimizations were followed by NMR calculations using the B3LYP/6-311+G(2d,p) density. Electrostatic potentials on the isodensity surface and electrostatically derived charges were generated via the Spartan program on an SGI Octane workstation As shown in FIG. 2, the distribution of electron density in 1 is strikingly different from that in 1C. In the former the area of lowest electropositive potential (50 kcal/mol) is associated with the B—H atoms, those being close to the imidazole ring. In 1C, the lowest potential (62 kcal/mol) is linked to the methyl H-atoms of the ring-appended neopentyl moiety. The latter are distal to the imidazole ring, which in both cations has the maximum electropositive potential at the $C^2$—H positions (116 and 127 kcal/mol respectively).

Differences are also observed in the electrostatically-derived charges of each ion. In 1, the charges on the three nitrogen atoms ($N^{im}$—Me, $N^{im}$—$BH_2$ and $N^{amine}$) are 0.23, 0.23 and 0.36 au, respectively. In 1C, a much larger localized charge (0.57 au) is carried by a single atom, the neopentyl methylene carbon, which is the structural counterpart of the $N^{amine}$ atom of 1. In turn, the imidazole N atoms of 1C are assigned smaller values (0.21 and 0.20) than their analogs in 1. Globally, the electronic differences between 1 and 1C are non-trivial and corroborate our initial supposition. Specifically, they suggest that the imidazole-boronium ion—like bis(amine)$BH_2^+$ cations—has a greater degree of charge delocalization than a conventional counterpart. J. H. Davis, Jr. and J. D. Madura *Tetrahedron Lett.* 1996, 37, 2729. We note that a high degree of charge delocalization is frequently regarded as contributing to the formation of ionic liquids.

NMR Spectral Studies. The $^{13}C$-, $^{11}B$- and $^{19}F$-NMR spectra of the boronium IL are unremarkable and comport with established data on other boronium ions and imidazolium $Tf_2N$-salts. A. G. Avent, P. A. Chalconer, M. P. Day, K. R. Seddon and T. Welton *J. Chem. Soc., Dalton Trans.* 1994, 3405; A. Elaiwi, P. B. Hitchcock, K. R. Seddon, N. Srinivasan, Y. M. Tan, T. Welton and J. A. Zora *J. Chem. Soc., Dalton Trans.* 1995, 3467; and P. Bonhote, A.-P. Dias, N. Papageorgiou, K. Kalyanasundaram and M. Gratzel *Inorg. Chem.* 1996, 35, 1168. However, the $^1$H-NMR spectra of the compounds exhibit a major difference compared to those of conventional imidazolium IL. Specifically, there is a marked dissimilarity in the absolute same-anion imidazole ring-H δ values for the boronium systems versus those of normal imidazolium IL. Notably, the $C^2$—H 6 of the boronium I-salts is in the 9-9.5 range, while for the compounds shown in Table 1 this resonance is just above 8 ppm. These values are significantly shifted from those of observed in same-anion conventional imidazolium salts. For example, in 1 the $C^2$—H resonance is at 8.14 ppm, while those in [$C_1$mim]$Tf_2N$ and [$C_2$mim]$Tf_2N$ are at 8.94 and 9.03 ppm respectively, differences of 0.80 and 0.89 δ. The $C^2$—H in the iodide salt of the same boronium cation comes at 9.09 ppm. Such results are highly suggestive of weaker solution state cation-anion H-bonding in the boronium salts than in common imidazolium IL and are in accord with both the X-Ray results and the lower electropositive potential computed for $C^2$—H in 1 versus 1C.

The $^1$H-NMR study of 3 revealed another anomaly as well, namely that the cation exists as a mixture of closely related structures. After an exhaustive multinuclear and multidimensional NMR study of this system, the data points to the existence of two forms of the cation of IL 3 which do not interconvert at room temperature. Further, based upon NOE experiments we believe that these are conformers, one of which has the amine-borane substituent in a thermodynamically preferred "over ring" conformation as seen in the solid-state structure of 1. The other is proposed to be a kinetic product in which the borane-amine substituent is interdigitated with and in roughly the same plane as the imidazole ring.

Applications of Ionic Liquids. Because of their unique properties and the ability to fine tune an ionic liquid to a particular need, ionic liquids have a wide array of applications. An incomplete list of beneficial properties of ionic liquids includes: no vapor pressure, reasonable thermal stability, good solubility for organic and organometallic compounds, gas solubility (CO, $O_2$, $H_2$, and the like) is good, can be immiscible with alkanes, tunable solvent properties (solubility, polarity, etc.), non-coordinating solvent, electrically conducting, low viscosity, low toxicity, good electrochemical stability, and, in the case of lipophilic room temperature ionic liquids, they can be used with aqueous biphasic systems.

Ionic liquids have been used in a number of broad and varied areas including the following non-limiting examples: 1) energy, which encompasses batteries, fuel cells, photovoltaic cells, heat storage (based on the large evolution of heat upon crystallization), and supercaps; 2) coatings, which encompasses metal depositions, analytic, lubricants, and surfactants; 3) chemical, which encompasses organic synthesis, chiral synthesis, polymerization, and catalysis; 4) biotechnology, which encompasses enzyme reactions and purification of proteins; 5) chemical engineering, which encompasses extractions, separations, membranes, and extractive distillations; and 6) other, which encompasses light emitting electrochemical cells (LECs), liquid crystals, nano particles, artificial muscles, oils/advanced fluids, and electrosynthesis of conducting polymers.

Ionic liquids that preferentially dissolve certain gaseous species can be used in conventional gas absorption applications. The non-volatile nature of ionic liquids plays two important roles. First, there will be no cross-contamination of the gas stream by the solvent during operation. This means no solvent loss and no air pollution. Second, regeneration of the solvent is easy; a simple flash or mild distillation step is all that is required to remove the gas from the solvent, again with no cross-contamination.

In addition to their use as conventional absorbents, ionic liquids may be immobilized on a support and used in a supported liquid membrane (SLM). The membrane will work if a gas preferentially dissolves in the liquid. SLMs may be used in a continuous separation process without a regeneration step. Conventional SLM technology is undermined by the fact that the liquid in which the gas dissolves eventually evaporates, thus rendering the membrane useless. Since ionic liquids are completely non-volatile, this problem is eliminated.

Ionic liquids also find use in the conversion of brown coal and oil shale into value-added products, such as alternative synthetic fuels and/or high-quality chemical feedstocks. For example, 1-butyl-3-methyl imidazolium, has been used to extract organic compounds from Estonian oil shale kerogen at various temperatures. Results at 175° C. yielded soluble products with an increase of ten times over that obtained using conventional organic solvents.

Brönsted-acidic ILs also act as proton shuttles, functionally carrying protons from acidic resin surfaces (e.g., Nafion) to the surrounding medium, where they are more free to react than if the proton is held at the polymer surface. Moreover, the Brönsted-acidic ILs have absolutely no vapor pressure when dissolved in water. For example, a relatively concentrated solution of HCl gives off HCl gas; in contrast, a Brönsted-acidic IL gives off no gaseous acid—pH paper suspended above the surface does not change colors.

Many product streams, particularly in the field of petroleum chemistry, include olefins and non-olefins. For example, ethane crackers tend to produce a mixture of ethane and ethylene. The ethylene is typically separated from the ethane via distillation. Because the boiling points of ethylene and ethane are relatively close to one another, the distillation is typically done at very low temperatures and/or high pressures; the separation is relatively expensive. The same problems are observed when separating propane from propylene in dehydrogenation facilities. Ionic liquids are useful is separating such mixtures. For example, an ionic liquid with a pendant functional group that coordinates the pi-bond of an olefin may be used to dissolve selectively the olefinic components of such a mixture. Likewise, an ionic liquid with a pendant functional group that coordinates a transition metal capable of coordinating the pi-bond of an olefin may be used to dissolve selectively the olefinic components of such a mixture. In either case, the dissolved olefins subsequently can be isolated by desorption.

The chemical field has made good use of ionic liquids where the potential for even greater use is constantly being explored. Known chemical reactions carried out in ionic liquids include butene oligomerization, hydrodimerization of dienes, alkylation of olefins, hydrogenation (e.g. of cyclohexene), hydroformylation, oxidation (e.g. epoxidation of 2,2-dimethyl chromene), alkoxycarbonylation (of styrene), and hydrodimerizations/telomerizations (e.g. of 1,3-butadiene). An advantage to using ionic liquids as the medium for chemical reactions is that the rates and selectivities can be modified by modifying the ionic liquid. Reaction mechanisms are similar to those in organic solvents.

In particular, research published since the early 1990's points to significant opportunities to replace solution polymerizations using VOCs with ionic liquids. Polymerizations that have been carried out in ionic liquid mediums include homopolymerizations with faster rates and higher MW; living radical homopolymerization where the catalyst has been retained in the ionic liquid phase; statistical copolymerization which may create copolymers having monomer sequences not readily achievable using conventional solvents; and block copolymerization where ionic liquid routes may simplify, reduce cost of producing block copolymers with defined structures. In another related area, polymer-ionic liquid composites as new possible materials have been explored.

Separations is another area in particular that is making use of ionic liquids. Highlights in this area include liquid extractions of organics and metals from aqueous solutions; sulfur removal and selective separations by solubility, extractive distillation, etc. in hydrocarbon processing; gas separations where task-specific ionic liquids have been developed based on solubilities; solvent regeneration as applied to, for example, supercritical fluids, pervaporation, and distillations; supported liquid membranes; electrorefining; and analytical separations.

Significant academic and industrial interest has also been directed towards using ionic liquids in fuel technology with the potential for high-volume, energy saving applications. Highlights in this area include liquefaction, gasifaction, and chemical modification of solid fuels (e.g., coal, oil shale, kerogen, and the like); sweetening of sour gas; optimization for high-octane fuel additives; environmental removal of contaminants from waste streams; desulfurization of fossil fuels; and safer and more efficient nuclear fuel cycles.

Another particularly important aspect of the present invention is the possibility for these ionic liquids to dissolve other salts, in particular metallic salts, such as lithium salts, to give highly conductive solutions. In a similar manner, the ionic liquids, or their mixtures with other metallic salts, are excellent solvents or plasticizers for a great number of polymers, in particular those bearing polar or ionic functions. Liquid compounds as well as polymers plasticized by ionic mixtures behaving like solid electrolytes are applicable in electrochemistry to generators of the primary or secondary type, supercapacities, electrochromic systems, antistatic coatings, batteries or electroluminescent diodes.

Computations suggest that the boronium ionic liquids are more difficult to reduce, by about 0.5 V, than the conventional imidazolium ionic liquids. Therefore, the inventive boronium ionic liquids may be used as liquid electrolytes for electrical storage devices in any of the following forms: (1) liquid electrolytes consisting solely of the above-described ionic liquids or low-melting electrolyte salts for electrical storage devices (i.e., liquid electrolytes in which a nonaqueous organic solvent is not used), (2) electrolyte solutions obtained by adding an ion-conductive salt to above liquid electrolyte (1) (here too, a nonaqueous organic solvent is not used in the liquid electrolyte), (3) electrolyte solutions obtained by adding also a nonaqueous organic solvent to above electrolyte solution (2), and (4) electrolyte solutions containing at least one of the above-described ionic liquids or electrolytes for electrical storage devices in combination with a nonaqueous organic solvent.

Any nonaqueous organic solvent which is capable of dissolving the above-described ionic liquid or electrolyte salt and is stable within the working voltage range for electrical storage devices such as secondary batteries and electrical double-layer capacitors may be used without particular limitation. However, it is preferable for the nonaqueous organic solvent to be one having a large dielectric constant, a broad electrochemical stability range, a broad service temperature range and excellent safety.

Illustrative examples of suitable solvents include acyclic ethers such as dibutyl ether, 1,2-dimethoxyethane, 1,2-ethoxymethoxyethane, methyl diglyme, methyl triglyme, methyl tetraglyme, ethyl glyme, ethyl diglyme, butyl diglyme, and glycol ethers (e.g., ethyl cellosolve, ethyl carbitol, butyl cellosolve, butyl carbitol); cyclic ethers such as tetrahydrofuran, 2-methyltetrahydrofuran, 1,3-dioxolane and 4,4-dimethyl-1,3-dioxane; butyrolactones such as γ-butyrolactone, γ-valerolactone, δ-valerolactone, 3-methyl-1,3-oxazolidin-2-one and 3-ethyl-1,3-oxazolidin-2-one; and solvents commonly used in electrochemical devices, such as amide solvents (e.g., N-methylformamide, N,N-dimethylformamide, N-methylacetamide, N-methylpyrrolidinone), carbonate solvents (e.g., diethyl carbonate, dimethyl carbonate, ethyl methyl carbonate, propylene carbonate, ethylene carbonate, styrene carbonate), and imidazolidinone solvents (e.g., 1,3-dimethyl-2-imidazolidinone). Any one or mixtures of two or more of these solvents may be used.

The use of a mixed solvent which includes as a main component ethylene carbonate or propylene carbonate, or of one or a mixture of two or more solvents selected from among ethylene carbonate, propylene carbonate, vinylene carbonate, dimethyl carbonate, ethyl methyl carbonate and diethyl carbonate, is preferred.

When the above-described liquid electrolyte is used as a liquid electrolyte for electrical storage devices, in the form described in (1) above it is of course 100% ionic liquid. In above forms (2), (3) and (4), the concentration of ionic liquid or electrolyte salt in the solvent, while not subject to any particular limitation, may be about 0.1 to about 5.0 mol/L, or about 1.0 to about 4.0 mol/L. At a concentration of less than about 0.1 mol/L, energy loss may rise due to increased internal resistance. On the other hand, at a concentration higher than about 5.0 mol/L, if the electrolyte salt has a low solubility and a relatively high melting point, undesirable effects may arise at low temperatures, such as deposition of the salt and a decline in stability.

In certain embodiments, because the electrolyte salts for electrical storage devices of the invention have a better solubility in nonaqueous organic solvents than conventional electrolyte salts and some have a melting point no higher than 25° C., the electrolyte salt does not readily deposit out of solution at low temperatures even when used at a higher electrolyte salt concentration than is normally the practice.

In certain embodiments, an ion-conductive salt may be added to the liquid electrolyte.

In this case, the ion-conductive salt may be any that is capable of being used in electrical storage devices, such as lithium secondary cells, lithium ion secondary cells and electrical double-layer capacitors. Ion-conductive salts that may be used include alkali metal salts and quaternary ammonium salts.

Preferred alkali metal salts are lithium salts, sodium salts and potassium salts. Specific examples include: lithium salts such as lithium tetrafluoroborate, lithium hexafluorophosphate, lithium perchlorate, lithium trifluoromethanesulfonate, sulfonyl imide lithium salts, sulfonyl methide lithium salts, lithium acetate, lithium trifluoroacetate, lithium benzoate, lithium p-toluenesulfonate, lithium nitrate, lithium bromide, lithium iodide and lithium tetraphenylborate; sodium salts such as sodium perchlorate, sodium iodide, sodium tetrafluoroborate, sodium hexafluorophosphate, sodium trifluoromethanesulfonate and sodium bromide; and potassium salts such as potassium iodide, potassium tetrafluoroborate, potassium hexafluorophosphate and potassium trifluoromethanesulfonate. These ion-conductive salts may be used singly or as combinations of two or more thereof.

Quaternary ammonium salts that may be used in electrical double-layer capacitors include tetramethylammonium hexafluorophosphate, tetraethylammonium hexafluorophosphate, tetrapropylammonium hexafluorophosphate, methyltriethylammonium hexafluorophosphate, tetraethylammonium tetrafluoroborate and tetraethylammonium perchlorate; and also acylic amidines, cyclic amidines (e.g., imidazoles, imidazolines, pyrimidines, 1,5-diazabicyclo[4.3.0]non-5-ene (DBN), 1,8-diazabicyclo[5.4.0]undec-7-ene (DBU)), pyrroles, pyrazoles, oxazoles, thiazoles, oxadiazoles, thiadiazoles, triazoles, pyridines, pyrazines, triazines, pyrrolidines, morpholines, piperidines and piperazines.

The ion-conductive salt has a concentration in the electrolyte solution of generally about 0.05 to about 3 mol/L, and preferably about 0.1 to about 2 mol/L. Too low an ion-conductive salt concentration may make it impossible to obtain a sufficient ionic conductivity, whereas too high a concentration may prevent complete dissolution in the liquid electrolyte.

Further discussion of the use of ionic liquids as electrolyte salts for storage devices, electronic double layer capacitors and secondary batteries can be found in, for example, Sato, T. et al. (United States Patent Application Publication No. US 2004/0094741A1); Koch et al. (U.S. Pat. No. 5,827,602); and McBreen, J. et al. (*Journal of Power Sources* 2000, 89, 163-167); all of which are hereby incorporated by reference in their entirety.

Ionic liquids of the present invention may also be used as surfactants. Surfactants are soluble chemical compounds that when added to a mixture of two liquids reduce the surface tension between said liquids. Although surfactant aggregation is usually studied in aqueous solutions, it also occurs in structured non-aqueous solvents such as room temperature ionic liquids (J. L. Anderson, V. Pino, E. C. Hagberg, V. V. Sheares, and D. W. Armstrong, *Chem. Comm*, 2003, 2444-2445). In one embodiment of the invention, the boronium ionic liquids of the invention are substituted with alkyl chains which provide surfactant-like properties to the cation. These alkyl group can be straight chain or branched and may include one or more substituents and pendant groups. A large number of other substituents may also be present.

Ionic liquids of the present invention may also be used as NMR shift reagents. Paramagnetic shift reagents have the ability to induce chemical shifts and thus simplify complex NMR spectra. Traditionally complexes of paramagnetic lanthanide ions such as europium(III) have been used for down field shifts and complexes of praseodymium(III) have been used for upfield shifts. In certain embodiments of the invention, boronium ionic liquids can be used as NMR shirt reagents.

Ionic liquids of the present invention may also be used as nitrogen protecting groups. When one of the amines bonded to the boron in the boronium ionic liquids is a compound of interest, the boron acts as a protecting group for said amine. Given the ease of synthesis and the orthogonally to other more traditional protecting groups, the compounds of the invention serve as novel means by which to protect a nitrogen-containing functionality.

Ionic liquids of the present invention may also be used as antimicrobial coatings. A wide range of antimicrobial agents have been applied to surfaces: antibiotics including chlorhexidine, rifampin and monocycline and others, silver/silver ions/silver compounds, hydantoin (also known as halamine) compounds, furanone compounds, and quaternary ammonium or phosphonium polymers. There have been a smaller number of non-permanently cationic antimicrobial polymeric materials prepared for use on surfaces, generally incorporating benzoic acid derivatives. The various agents are most often physically applied to the surface, physically impregnated into the bulk of the material, or physically incorporated into a coating that is then applied to the surface for "controlled release". Given the cationic nature of the ionic liquids of the invention they may find use as antimicrobial coatings.

Methods of the Invention. One aspect of the present invention is a method of removing an alkene, alkyne or carbon monoxide from a mixture, comprising the step of exposing a mixture to a complex formed from a transition metal and a salt; wherein said salt is represented by formula I-VIII.

Another aspect of the present invention is a method of removing carbon dioxide, carbonyl sulfide, sulfur dioxide, sulfur trioxide, hydrogen sulfide or a carbonyl-containing compound from a gaseous or liquid mixture, comprising the step of exposing a gaseous or liquid mixture to a salt represented by formula I-VIII.

Another aspect of the present invention is a method of transporting carbon dioxide, carbonyl sulfide, sulfur dioxide, sulfur trioxide, hydrogen sulfide or a carbonyl-containing compound from a first gaseous or liquid mixture to a second gaseous or liquid mixture, comprising the steps of exposing a first gaseous or liquid mixture to a salt represented by formula I-VIII; and subsequently exposing the salt to a second gaseous or liquid mixture, thereby transporting carbon dioxide, carbonyl sulfide, sulfur dioxide, sulfur trioxide, hydrogen sulfide or a carbonyl-containing compound to the second gaseous or liquid mixture:

In certain embodiments, the present invention relates to the aforementioned method and the attendant definitions, wherein said gaseous or liquid mixture is natural gas.

In certain embodiments, the present invention relates to the aforementioned method and the attendant definitions, wherein carbon dioxide is removed.

In certain embodiments, the present invention relates to the aforementioned method and the attendant definitions, wherein the salt is dissolved in water.

In certain embodiments, the present invention relates to the aforementioned method and the attendant definitions, wherein said salt is contained within a semi-permeable membrane.

Another aspect of the present invention is a method of preparing a solution, comprising the step of combining a solute and a solvent to produce a solution; wherein said solvent is a salt represented by formula I-VIII.

Another aspect of the present invention is a method of catalyzing a base-catalyzed chemical reaction to give a product, comprising the step of exposing a reactant mixture to a salt; wherein said salt is represented by formula I-VIII.

Another aspect of the present invention is a method of catalyzing an acid-catalyzed chemical reaction to give a product, comprising the step of exposing a reactant mixture to a salt; wherein said salt is represented by formula I-VIII.

In certain embodiments, the present invention relates to the aforementioned method and the attendant definitions, wherein said chemical reaction is acid-catalyzed.

In certain embodiments, the present invention relates to the aforementioned method and the attendant definitions, wherein said reactant mixture comprises an alcohol; and said product is an ether.

In certain embodiments, the present invention relates to the aforementioned method and the attendant definitions, wherein said reactant mixture comprises an alcohol and a carboxylic acid; and said product is an ester.

In certain embodiments, the present invention relates to the aforementioned method and the attendant definitions, wherein said reactant mixture comprises an ester and water; and said product is a carboxylic acid.

In certain embodiments, the present invention relates to the aforementioned method and the attendant definitions, wherein said reactant mixture comprises an alcohol and a first ester; and said product is a second ester.

In certain embodiments, the present invention relates to the aforementioned method and the attendant definitions, wherein said reactant mixture comprises a 1,2-diol; and said product is a ketone.

In certain embodiments, the present invention relates to the aforementioned method and the attendant definitions, wherein said reactant mixture comprises an alcohol; and said product is an alkene.

In certain embodiments, the present invention relates to the aforementioned method and the attendant definitions, wherein said reactant mixture comprises a first alkene; and said product is a second alkene.

In certain embodiments, the present invention relates to the aforementioned method and the attendant definitions, wherein said reactant mixture comprises a first aromatic compound and a nitrating agent; and said product is a second aromatic compound comprising a nitro group.

In certain embodiments, the present invention relates to the aforementioned method and the attendant definitions, wherein said reactant mixture comprises a first aromatic compound and an alcohol; and said product is a second aromatic compound comprising an alkyl group.

In certain embodiments, the present invention relates to the aforementioned method and the attendant definitions, wherein said reactant mixture comprises a first aromatic compound and a carboxylic acid; and said product is a second aromatic compound comprising an acyl group.

In certain embodiments, the present invention relates to the use of a boronium ionic liquid of the invention with an appended amine (e.g., primary, secondary, tertiary, or heterocyclic) for the capture from the gas phase of an acidic gas, including but not limited to $H_2S$, $CO_2$, COS, $SO_2$, and $SO_3$.

In certain embodiments, the present invention relates to the use of a boronium ionic liquid of the invention with an appended amine (e.g., primary, secondary, tertiary, or heterocyclic) in conjunction with water for the capture of an acidic gas from the gas phase.

In certain embodiments, the present invention relates to the use of a boronium ionic liquid of the invention with an appended amine (e.g., primary, secondary, tertiary, or heterocyclic) dissolved in a molecular solvent or other ionic liquid for the capture of an acidic gas from the gas phase.

In certain embodiments, the present invention relates to the use of a boronium ionic liquid of the invention with an appended amine dissolved in water or other solvent as a non-odorous, non-volatile base for a general-base-catalyzed reaction.

In certain embodiments, the present invention relates to the use of a boronium ionic liquid of the invention with an appended amine as a scavenging agent for an amine-reactive material in the solution phase.

In certain embodiments, the present invention relates to the use of a boronium ionic liquid of the invention with an appended amine as a solvent.

In certain embodiments, the present invention relates to the use of a boronium ionic liquid of the invention with an appended amine (e.g., primary, secondary, tertiary or heterocyclic) alone or in conjunction with an organic molecule, such as salicylaldehyde, for the extraction of a metal ion from an aqueous solution.

In certain embodiments, the present invention relates to the use of a boronium ionic liquid of the invention with an appended amine in conjunction with an ion-exchange resin, clay or zeolite for any of the aforementioned applications.

In certain embodiments, the present invention relates to the use of a boronium ionic liquid of the invention with an appended acidic group for general or specific acid catalysis, either as a pure material, or as a solution in another ionic liquid or molecular solvent. Such reactions include, but are not limited to, Fischer esterification, pinnacol rearrangement, alcohol dehydration, rearrangements, isomerizations, Friedel-Crafts alkylation and acylation, or aromatic nitration.

In certain embodiments, the present invention relates to the use of a boronium ionic liquid of the invention with an appended acidic group as a scavenging agent for an acid-reactive material in the gas or solution phase.

In certain embodiments, the present invention relates to the use of a boronium ionic liquid of the invention with an appended acidic group as a dehydrating or drying agent.

In certain embodiments, the present invention relates to the use of a boronium ionic liquid of the invention with an appended acid in conjunction with an ion-exchange resin, clay or zeolite for any of the aforementioned applications.

In certain embodiments, the present invention relates to the use of a boronium ionic liquid of the invention with an appended acidic group as a solvent.

In certain embodiments, the present invention relates to the use of a boronium ionic liquid of the invention with an appended fluoroketone or fluoroalcohol group as a solvent; as an acid; or as an activator of peroxide for use in an oxidation reaction.

In certain embodiments, the present invention relates to the use of a boronium ionic liquid of the invention with an appended sulfone, sulfoxide or sulfonamide group in a liquid-liquid or liquid-gas separation, including a separation in the refining of petroleum or petrochemicals.

In certain embodiments, the present invention relates to the use of a boronium ionic liquid of the invention with an appended sulfone, sulfoxide or sulfonamide group as a solvent for a polar molecule, including but not limited to biomolecules, such as saccharides, amino acids, nucleic acids, proteins, enzymes, DNA and RNA.

In certain embodiments, the present invention relates to the use of a boronium ionic liquid of the invention with an appended sulfone, sulfoxide or sulfonamide group as a solvent.

In certain embodiments, the present invention relates to the use of a boronium ionic liquid of the invention with an appended sulfone, sulfoxide or sulfonamide group as a phase-transfer adjuvant for use in conjunction with a supercritical solvent, e.g., supercritical $CO_2$.

In certain embodiments, the present invention relates to the use of a boronium ionic liquid with an appended sulfonyl halide group as a scavenging reagent for use in conjunction with a reactive species.

In certain embodiments, the present invention relates to the use of a boronium ionic liquid of the invention with an appended sulfone or sulfoxide group in conjunction with ion exchangeable materials, such as ion exchange resins, clays, and zeolites, for any of the aforementioned uses.

In certain embodiments, the present invention relates to the use of a boronium ionic liquid of the invention with an appended amide, urea or thiourea group in a liquid-liquid or liquid-gas separation, including separations in the refining of petroleum or petrochemicals.

In certain embodiments, the present invention relates to the use of a boronium ionic liquid of the invention with an appended amide, urea or thiourea group as a solvent for a polar molecule, including but not limited to biomolecules, such as saccharides, amino acids, nucleic acids, proteins, enzymes, DNA and RNA.

In certain embodiments, the present invention relates to the use of a boronium ionic liquid of the invention with an appended amide, urea or thiourea group as a solvent.

In certain embodiments, the present invention relates to the use of a boronium ionic liquid of the invention with an appended amide, urea or thiourea group in conjunction with an ion exchangeable material, such as ion exchange resins, clays, and zeolites, for any of the aforementioned uses.

In certain embodiments, the present invention relates to the use of a boronium ionic liquid of the invention with an appended amide, urea or thiourea group as a phase-transfer adjuvant for use in conjunction with a supercritical solvent, e.g., supercritical $CO_2$.

In certain embodiments, the present invention relates to the use of a phosphoramide appended boronium ionic liquid of the invention, alone or in conjunction with another ionic liquid or a molecular solvent, as a solvent or for the extraction of a metal from an ore or immiscible solution phase.

In certain embodiments, the present invention relates to the use of a functionalized boronium ionic liquid of the invention as a solvent, reagent-solvent, or a catalyst-solvent for a polymerization or a polymer-processing operation.

In certain embodiments, the present invention relates to the use of a functionalized boronium ionic liquid of the invention as an anti-static agent, e.g., in a solution, petroleum or a petrochemical.

Another aspect of the present invention is an electrolyte for use in an electrochemical cell comprising the ionic liquid of formula I-VIII; and a polar organic liquid.

In certain embodiments, the present invention relates to the aforementioned electrolyte, wherein said polar organic liquid is selected from the group consisting of linear ethers, cyclic ethers, esters, carbonates, lactones, nitrites, amides, sulfones and sulfolanes.

In certain embodiments, the present invention relates to the aforementioned electrolyte, wherein said polar organic liquid is selected from the group consisting of diethylether, dimethoxyethane, tetrahydrofuran, dioxane, dioxolane, methyltetrahydrofuran, methyl formate, ethyl formate, methyl propionate, propylene carbonate, ethylene carbonate, dimethyl carbonate, diethyl carbonate, ethylmethyl carbonate, dibutyl carbonate, butyrolactones, acetonitrile, benzonitrile, nitromethane, nitrobenzene, dimethylformamide, N-methylpyrrolidone, dimethylsulfone, tetramethylene sulfone, sulfolane and thiophene.

Another aspect of the present invention is an electrochemical cell comprising an anode; a cathode; and an electrolyte comprising the ionic liquid of formula I-VIII.

Another aspect of the present invention is an electrochemical cell comprising an anode; a cathode; and an electrolyte comprising the ionic liquid of formula I-VIII. and a lithium salt.

In certain embodiments, the present invention relates to the aforementioned electrochemical cell, wherein said electrolyte further comprises a polar organic liquid.

Another aspect of the present invention is a capacitor comprising a first electrode; a second electrode; and an electrolyte, said electrolyte comprising an ionic liquid of formula I-VIII.

In certain embodiments, the present invention relates to the aforementioned capacitor, wherein said electrolyte further comprises a polar organic liquid.

In certain embodiments, the present invention relates to the aforementioned capacitor, wherein said polar organic liquid is selected from the group consisting of linear ethers, cyclic ethers, esters, carbonates, lactones, nitrites, amides, sulfones and sulfolanes.

One aspect of the present invention is using an ionic liquid of formula I-VIII as a surfactant. In one embodiment the present invention relates to a method of preventing or decreasing an emulsion in a sample comprising the step of adding an ionic liquid of formula I-VIII to said sample.

Another aspect of the present invention is an antimicrobial coating consisting of an ionic liquid of formula I-VIII. Another aspect of the present invention is an antimicrobial ointment or powder consisting of an ionic liquid of formula I-VIII. Another aspect of the present invention is the method of slowing or halting the growth of a bacteria comprising the step of exposing said bacteria to an ionic liquid of formula I-VIII.

Another aspect of the present invention is the method of shifting resonance signals in a NMR spectra of a sample comprising the step of adding an ionic liquid of formula I-VIII into said sample.

Another aspect of the present invention is using an ionic liquid of formula I-VIII as a protecting group for a nitrogen-containing functionality.

EXEMPLIFICATION

The invention now being generally described, it will be more readily understood by reference to the following examples, which are included merely for purposes of illustration of certain aspects and embodiments of the present invention, and are not intended to limit the invention.

Example 1

Preparation of [(1-methylimidazole)(trimethylamine)BH$_2$]$^+$I$^-$

A 500 mL flask was charged with a magnetic stirbar and purged with dry nitrogen.[1] While maintaining the nitrogen atmosphere, 250 mL of anhydrous benzene was added. To the benzene was added 14.60 g (0.20 mol) of trimethylamine-borane complex (purchased from Aldrich Chemical Co.). Once the complex had completely dissolved, 23.11 g (0.11 mol of I$_2$, 0.22 mol I atom) of I$_2$ was added in small portions over a ten-minute period of time, all the while maintaining a slow purge of nitrogen gas through the system. After stirring for an additional 30 min, the solution remained slightly red-brown.[2] To the stirred solution of Me$_3$N—BH$_2$I thus prepared was then added in one portion 7.47 g (0.44 mol) 1-methylimidazole.[3,4] Within a few minutes a white solid had begun to precipitate.[5] The precipitation was accompanied by a moderate exotherm, which was controlled by cooling in an icebath.[6] After cooling for 30 min, the solid was separated by suction filtration in air.[8] The solid was washed with small portions of benzene and ether then dried in vacuo. Yield: 47.83 g (85% based upon trimethylamine-borane).

Notes (generally applicable to all subsequent synthetic procedures described herein)
1. Repeat preparations were run variously in air or under nitrogen, with yields in the nitrogen reactions usually being slightly higher.
2. In repeat reactions the solution was at this stage colored at times and colorless on other occasions. No consistent variation in yield or product purity appears to be manifest as function of this phenomenon.
3. Extensive subsequent experimentation determined that the use of an excess of alkyl imidazole (heterocycle) was unnecessary and in some cases undesirable, leading to difficulties in isolating pure products. This is especially the case where the imidazole is relatively lipophilic (e.g., 1-butylimidazole or 1-decyl-2-methylimidazole, where the boronium salts formed remained soluble or partially soluble in the benzene phase rather than cleanly precipitating as in the case of the present example. In these cases, removal of excess imidazole from the product boronium salts may be accomplished but only after exhaustive extraction or tedious chromatographic processes. It should also be noted that symmetrical bis(tertiary amine)BH$_2$$^+$ and bis(heterocycle)BH$_2$$^+$ compounds may be prepared using similar approaches.
4. Other heterocycles or substituted imidazoles successfully used to date include (but are not limited to) optionally substituted 3- and 4-methyl thiazole, 3-butyl pyridine, 3-picoline, 4-picoline, butyl nicotinate, 1,2-dimethyl imidazole, and miconazole. Other amine-boranes successfully used include (but are not limited to) tributylamine-borane, dimethyldodecylamine-borane and tropane-borane. One particularly interesting variation on this theme involves the use of the borane complex of dimethyldodecyl amine. Using this as the amine-borane complex in conjunction with pyridine as the heterocycle gives rise to a cation which is isoelectronic and isostructural to a representative of the class of quaternary ammonium cations known collective as benzalkonium chlorides, a widely used class of anti-microbial compound.
5. Repeat syntheses of this material, as well as syntheses of other boronium ions were sometimes characterized by a completely colorless solution at this stage; at other times a slight red-brown color was still present. Yields of product do not appear to vary as a function of this solution color.
6. The iodide salt thus isolated does not appear to be hygroscopic or air sensitive.
7. In syntheses where only one equivalent of heterocycle was used (see note 3), the exotherm was less marked to non-existant. In these cases, stirring was continued for longer periods of time (1-12 h) prior to work-up.
8. In procedures involving more lipophilic heterocycles (e.g., 1-butylimidazole) the iodide salt usually separates as a colorless (dense) liquid phase which is separated from the organic phase by decantation. This phase is subsequently washed with additional portions of benzene then ether before all volatiles are removed using rotary evaporation then a mechanical vacuum pump. A number of the iodide salts remain as supercooled liquids for prolonged periods, though we have yet to find one which does not eventually crystallize.

Example 2

Preparation of [(1-methylimidazole)(trimethylamine)BH$_2$]$^+$Tf$_2$N$^-$

In a 100 mL Erlenmeyer flask charged with a magnetic stirbar, 2.54 g of [(1-methylimidazole)(trimethylamine)BH$_2$]$^+$I$^-$ was dissolved in 25 mL of deionized water. To the stirred solution was added in one portion 3.43 g of lithium bis(trifluoromethanesulfonyl)amide, the dissolution of which into the water was accompanied by a near-simultaneous separation from the water of a dense, colorless, second liquid phase. To this two-phase system was added 20 mL of chloroform, which admixed with the denser (boronium salt) phase. The water and organic phases were separated and the chloroform phase dried with a small quantity of anhydrous magnesium sulfate. The latter was then removed by filtration and the chloroform evaporated under reduced pressure. It remained as a stable supercooled phase for several days before slowly crystallizing into a colorless mass (mp=60.2° C. by DSC, scan rate 10° C./min). Bis(trifyl)amide salts of other boronium cations are prepared similarly, and all to date have proven to be persistent room-temperature ionic liquids. The corresponding PF$_6$$^-$ and BF$_4$$^-$ salts of a number of these cations have also been prepared, several of them also being RTIL, although all are visibly more viscous than same-cation salts of the Tf$_2$N$^-$ anion.

Example 3

Preparation of [(1-butylimidazole)(triethylamine)BH$_2$]$^+$I$^-$

A 500 mL flask was charged with a magnetic stirbar and purged with dry nitrogen. While maintaining the nitrogen atmosphere, 250 mL of anhydrous benzene was added. To the benzene was added 11.99 g (0.10 mol) of triethylamine-borane complex (purchased from Aldrich Chemical Co.). Once the complex had completely dissolved, 13.23 g (0.10 mole of I$_2$, 0.21 mole of I atom) of I$_2$ was added in small portions over a ten-minute period of time, all the while maintaining a slow purge of nitrogen gas through the system. After stirring for an additional 30 min, the solution was pale yellow. To the stirred solution of Et$_3$N—BH$_2$I thus prepared was then added in one portion 13.4 g (0.11 mol) 1-butylimidazole. The solution immediate became nearly colorless, and within a few minutes a second colorless liquid layer had formed which was more dense than the benzene solvent. After stirring for four hours, the two liquid layers were separated. The lower salt layer was washed with benzene and ether. On cooling after rotary evaporation to remove residual solvent, the material became a colorless glass. Yield: 33.6 g (92% based upon triethylamine-borane).

Example 4

Preparation of [(1-butylimidazole)(triethylamine)$BH_2$]$^+Tf_2N^-$

In a 100 mL Erlenmeyer flask charged with a magnetic stirbar, 13.3 g (0.036 mol) of [(1-butylimidazole)(triethylamine)$BH_2$]$^+I^-$ was dissolved in 100 mL of deionized water. To the stirred solution was added in one portion 8.95 g of sodium bis(trifluoromethanesulfonyl)amide (0.036 mol), the dissolution of which into the water was accompanied by a near-simultaneous separation from the water of a dense, colorless, second liquid phase. The lower phase was removed from the aqueous phase by decantation then dissolved in 50 mL of methanol. The methanol solution was dried with anhydrous magnesium sulfate, filtered and evaporated in vacuo, producing a clear, colorless liquid product (16.3 g, 96%).

Example 5

Preparation of [(1-decyl-2-methylimidazole)$_3$BH]$^+$$_2$.2Br$^-$

A 250 mL flask fitted with a reflux condenser was charged with a magnetic stirbar and purged with dry nitrogen.[1] While maintaining the nitrogen atmosphere, 50 mL of anhydrous toluene was added. To the toluene was added 5 mL g (0.020 mol) of 1-decyl-2-methylimidazole. To this was added in one portion 1.6 g (0.007 mol) dibromoborane-methyl sulfide complex (purchased from Aldrich Chemical Co.). The solution was heated to reflux for 12 h, during which time a yellow oil separated from solution. The oil was separated by decantation and washed with a minimal quantity of ether before being dried in vacuo. Yield: 4.2 g (74%). When dissolved in water at concentrations down to at least as low as 1 mM, this material exhibits surfactant properties, facilitating the formation of foams upon agitation.

Example 6

Preparation of [(1-decyl-2-methylimidazole)$_3$BH]$^+$$_2$.2Tf$_2$N$^-$

In a 100 mL Erlenmeyer flask charged with a magnetic stirbar, 1.5 g of [(1-decyl-2-methyl)$_3$BH]$^{+2}$.2Br$^-$ was dissolved in 25 mL of deionized water. To the stirred solution was added in one portion 0.800 g (0.003 mol, 40% excess) of lithium bis(trifluoromethanesulfonyl)-amide, the dissolution of which into the water was accompanied by a near-simultaneous separation from the water of a thick, pale yellow oil. The water phase was removed by decantation and the residue dissolved in methanol, dried with anhydrous magnesium sulfate and filtered. Removal of the solvent in vacuo gave a pasty, pale-yellow product (1.32 g, 90%).

Example 7

Preparation of [(1,2-dimethylimidazole)$_2$BH$_2$]+ Tf$_2$N$^-$

A 500 mL flask fitted with a reflux condenser was charged with a magnetic stirbar and purged with dry nitrogen.[1] While maintaining the nitrogen atmosphere, 200 mL of anhydrous toluene was added. To the toluene was added 40 mL g (0.020 mol) of a 2.1M solution of monobromoborane-methyl sulfide complex in toluene (purchased commercially from Aldrich Chemical Co.) To this was added in one portion 8.1 g 1,2-dimethylimidazole. The resulting solution was heated to reflux for 12 h, during which time a colorless oil separated from solution. The upper organic layer was separated by decantation and the product washed with ether then dried in vacuo. A 6.58 g sample of the product bromide salt was then dissolved in 50 mL of water to which was then added 7.00 g of NaTf$_2$N. A second liquid layer formed immediately. This was dissolved in dichloromethane, dried with anhydrous magnesium sulfate and filtered. Removal of the solvent in vacuo gave a colorless oil, which gradually solidified to give 10.5 g of a low-melting, ivory colored solid product. When this procedure is repeated on the same scale using 1-methylimidazole, 1-butylimidazole (see X-ray structure below), or dimethyl-n-butyl amine room-temperature ionic liquids are obtained. Other amines used in this fashion (e.g., dimethyldodecyl amine) give products which are room-temperature semi-solids.

Example 8

Representative NMR Spectrum of an as-Isolated Boronium Ionic Liquid

Figure 5:
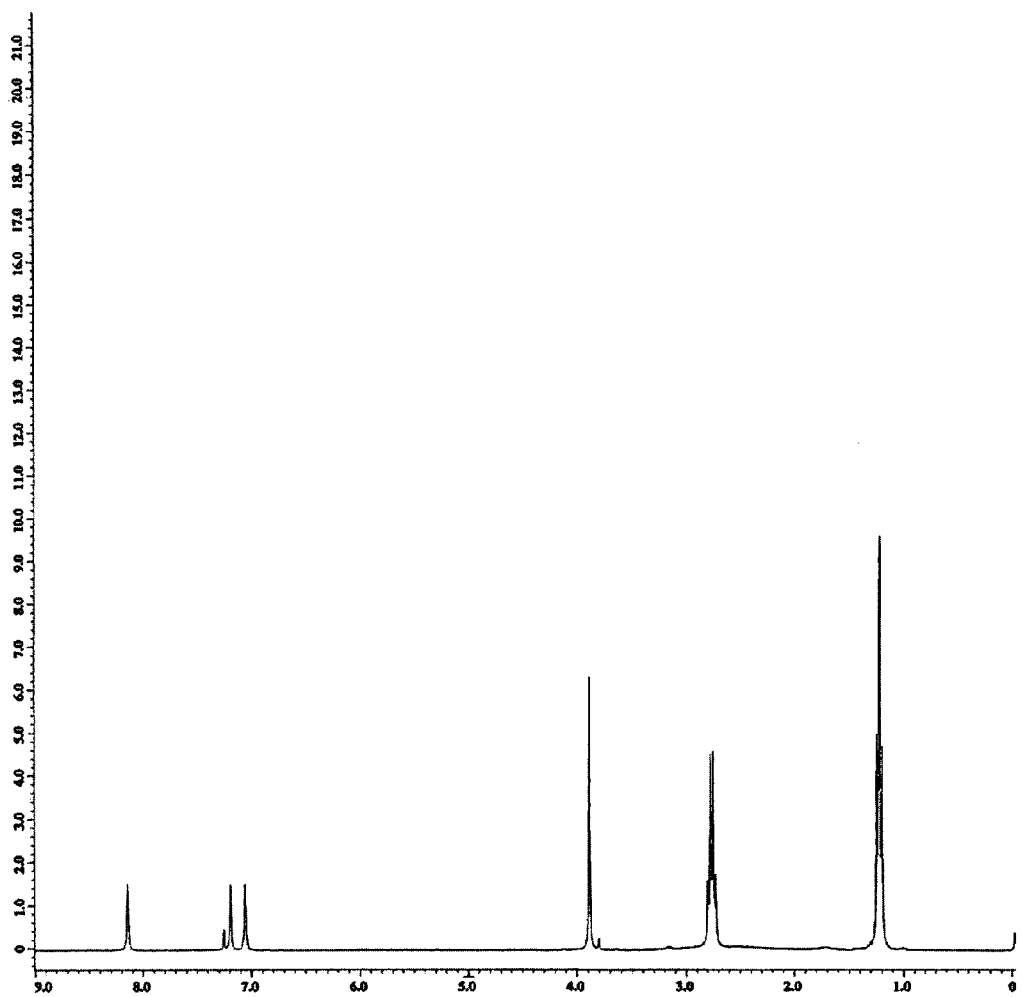
FIG. 5 depicts the $^1$H NMR spectrum of [(N-1-methylimidazole)(triethylamine)$BH_2]^{+1}Tf_2N^{-1}$ 2.
Figure 6:
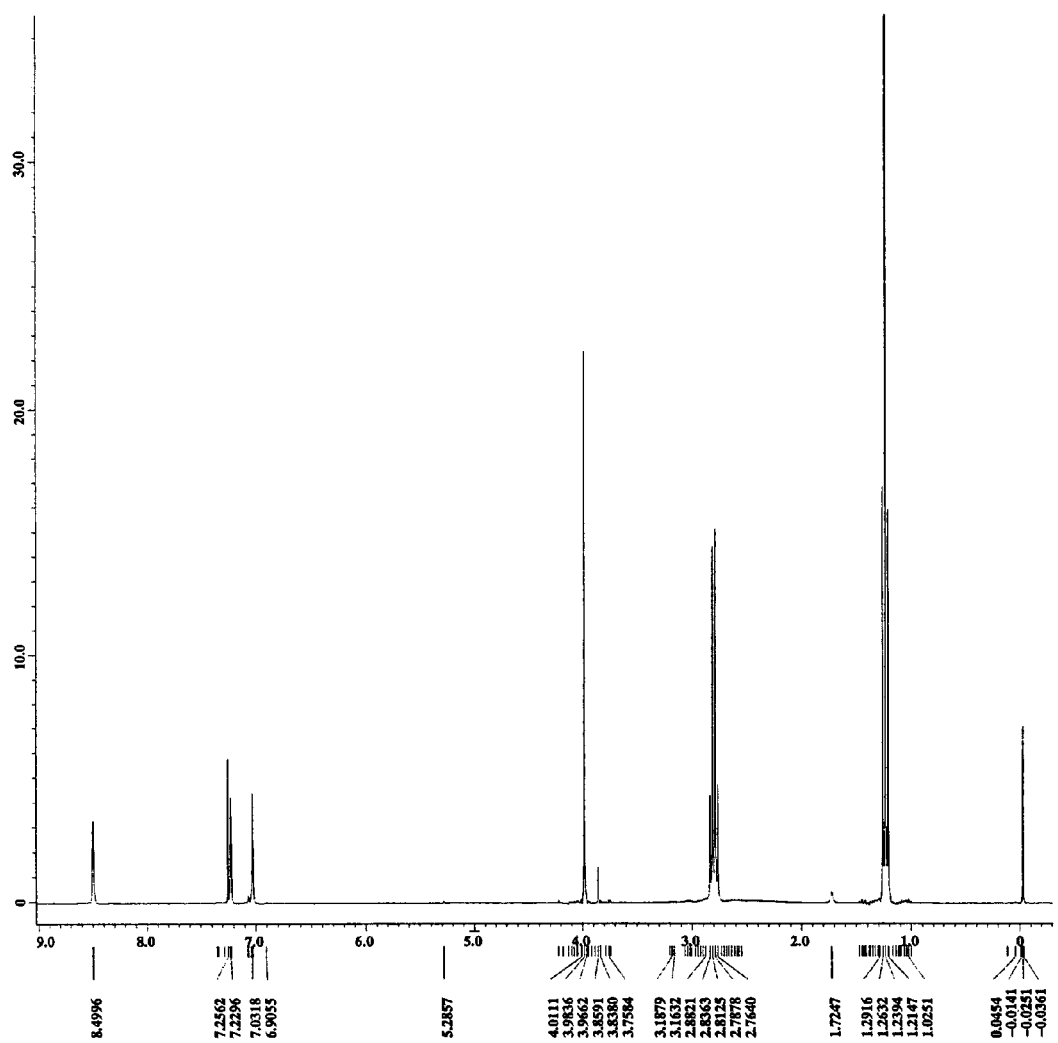
FIG. 6 depicts the $^1$H NMR spectrum of [(N-1-methylimidazole)(triethylamine)$BH_2]^{+1}BF_4^{-1}$.
Figure 7:
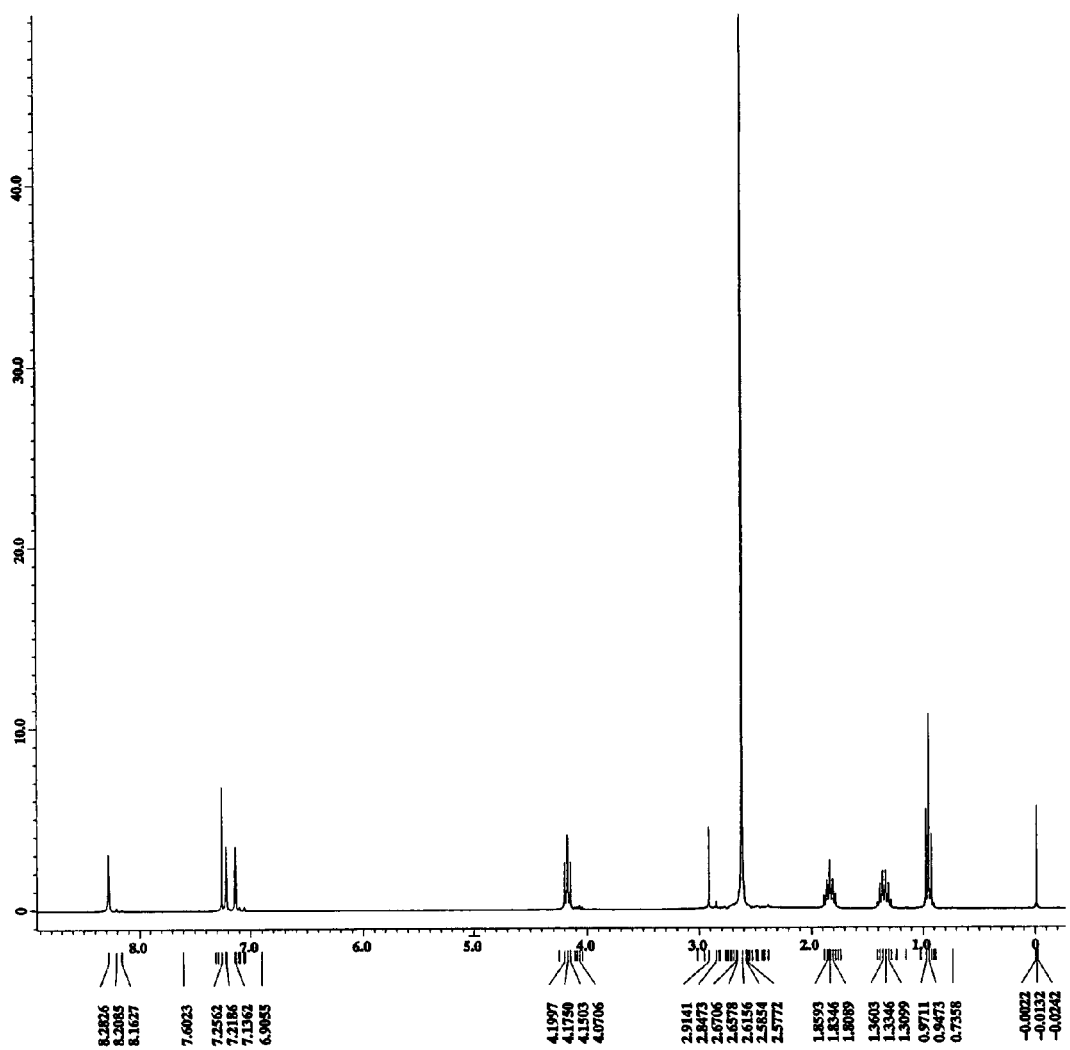
FIG. 7 depicts the $^1$H NMR spectrum of [(N-1-butylimidazole)(trimethylamine)$BH_2]^{+1}Tf_2N^{-1}$ 4.
Figure 8:
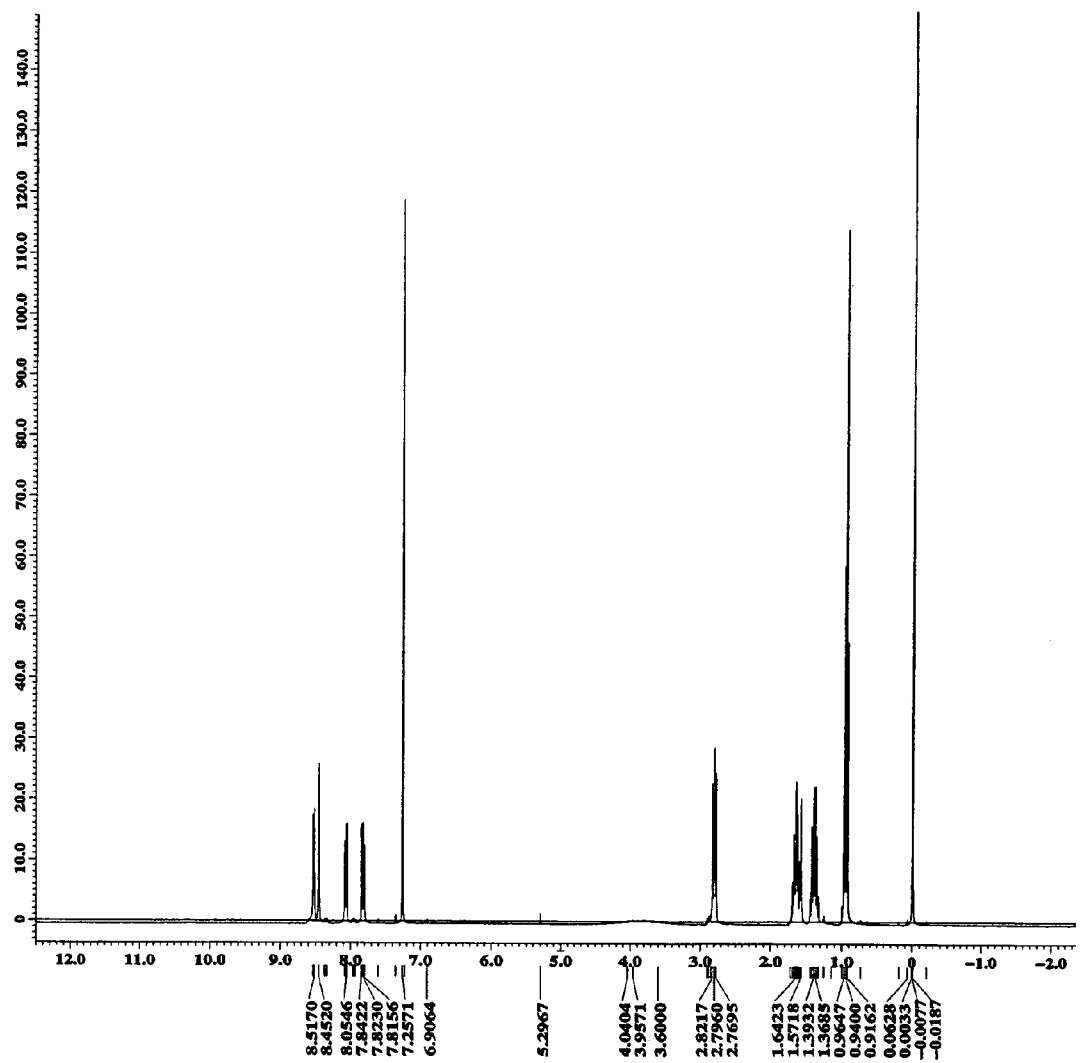
FIG. 8 depicts the $^1$H NMR spectrum of [(3-butylpyridine)$_2BH_2]^{+1}Tf_2N^{-1}$.
Figure 9:
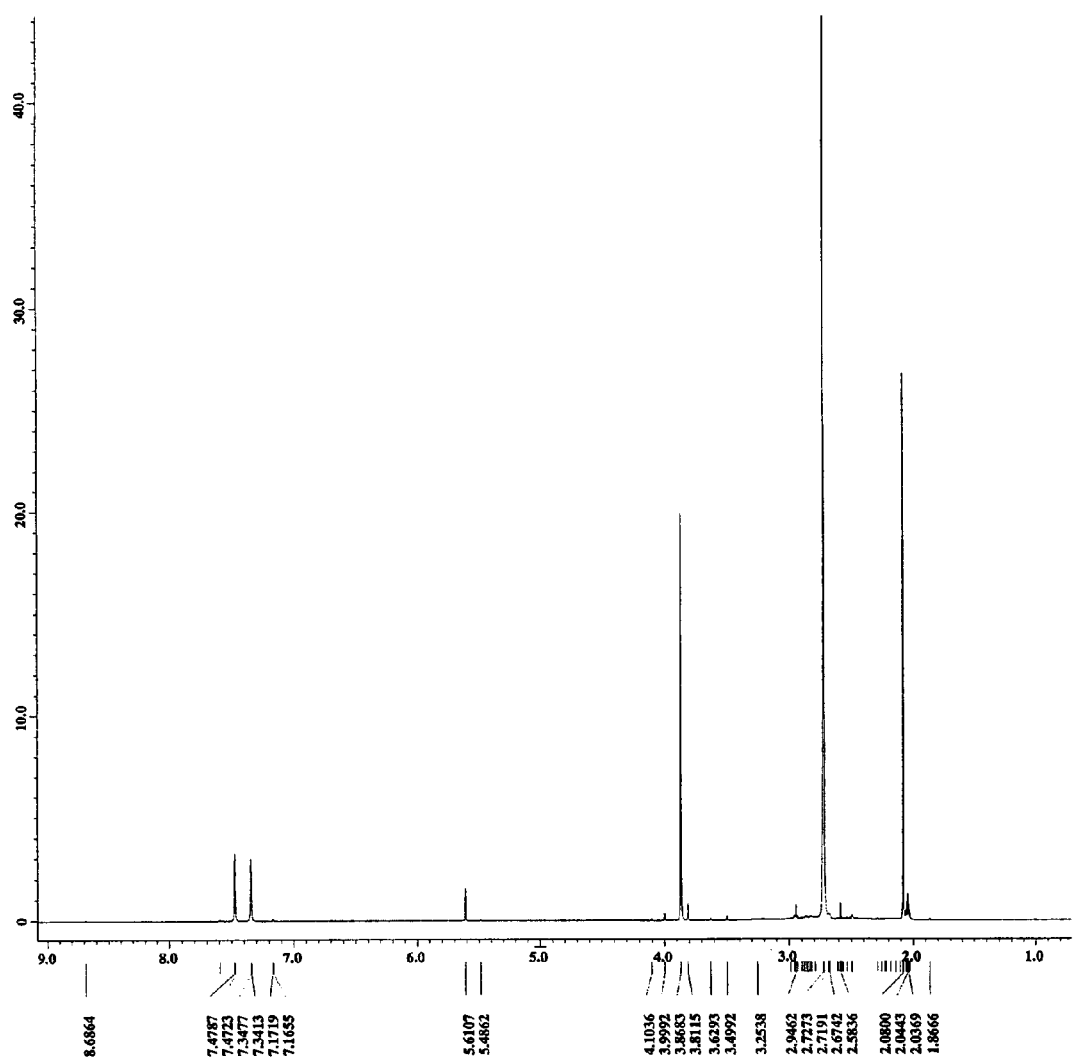
FIG. 9 depicts the $^1$H NMR spectrum of (N-1-methylimidazole)(trimethylamine)$BH_2]^{+1}Tf_2N^{-1}$ 1.
Figure 10:
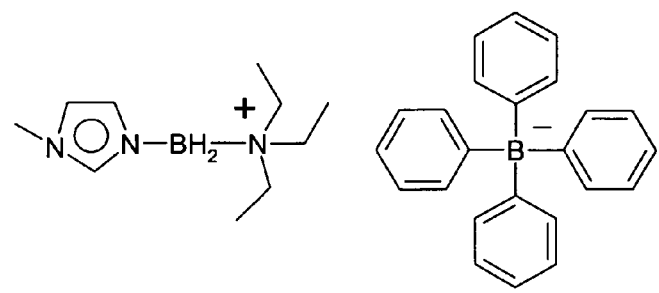
FIG. 10 depicts a representation of the X-ray structure of a tetraphenylboron salt of [(N-1-methylimidazole)(triethylamine)$BH_2]^{+1}BF_4^{-1}$.
Figure 10:
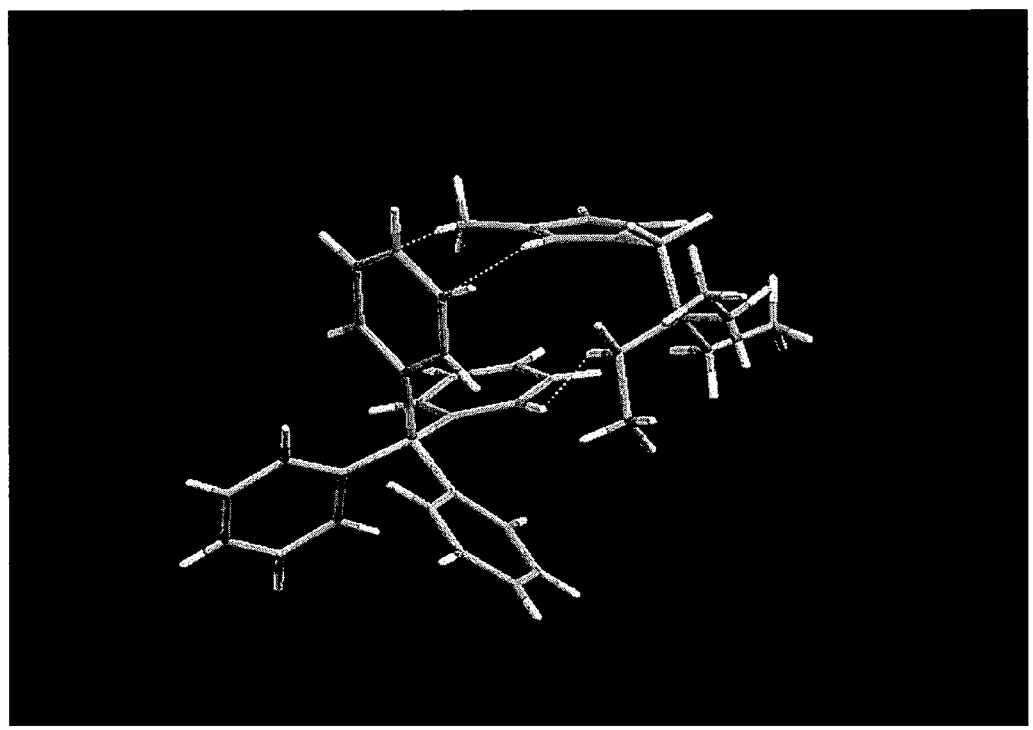
Figure 11:
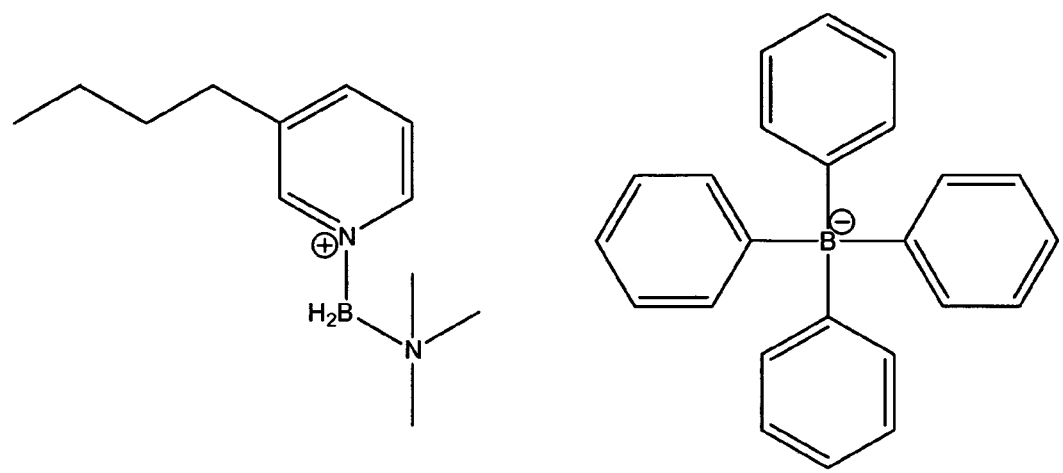
FIG. 11 depicts a representation of the X-ray structure of a tetraphenylboron salt of [(3-butylpyridine)(trimethyamine)$BH_2]^{+1}BPh_4^{-1}$. It is notable that the $Tf_2N^{-1}$ salt of this cation is a room-temperature liquid. In contrast, previous pyridinium salts with shorter (e.g., methyl) groups on the ring and different anions (e.g., $PF_6^-$) melt at much higher temperatures. This is a prime example of how in certain embodiments putting in longer chain alkyl groups and/or using different anions can lead to boronium salts with desirable properties.
Figure 11:
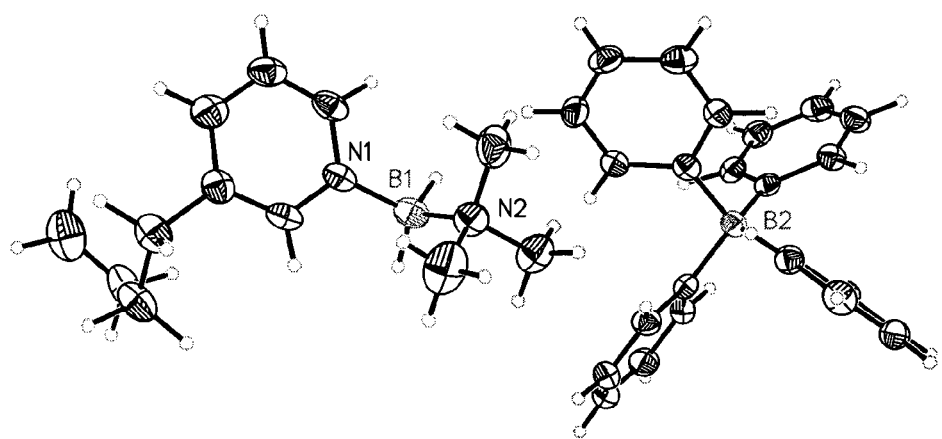
Figure 12:
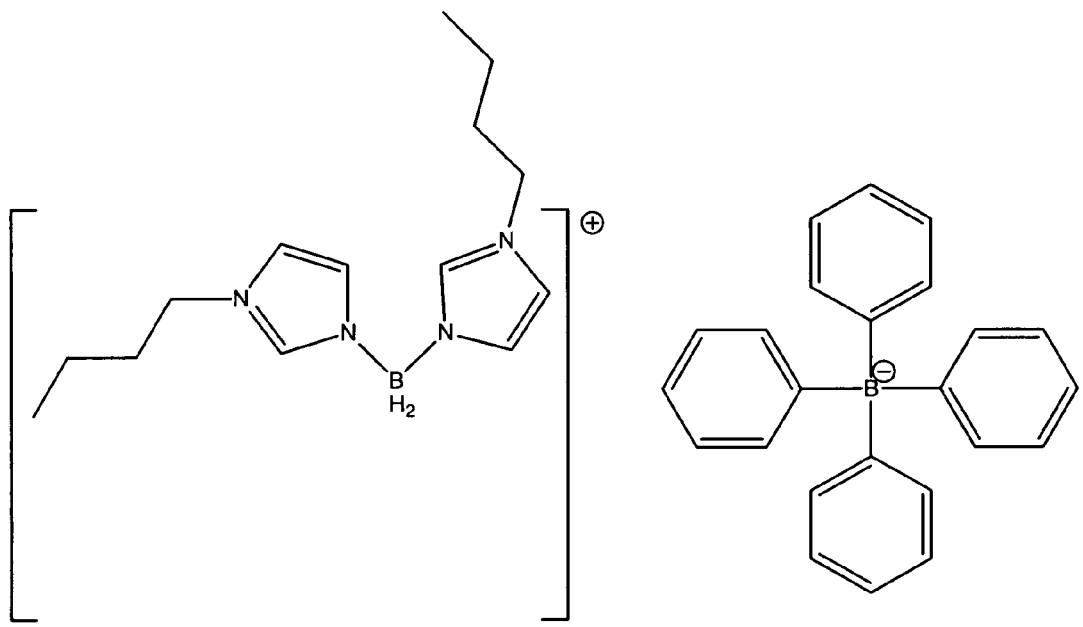
FIG. 12 depicts a representation of the crystal structure of the tetraphenylboron salt of [(N-1-butylimidazole)(trimethylamine)$BH_2]^{+1}BPh_4^{-1}$. The $Tf_2N^{-1}$ salt of this cation is also a room-temperature ionic liquid.
Figure 12:
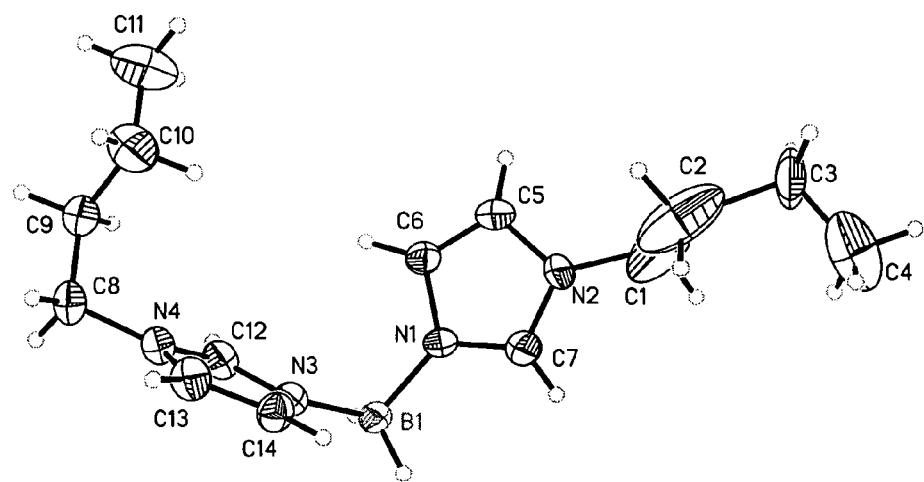

The $^1$H-NMR spectrum shown (FIG. 5) is of an as-isolated (non-chromatographed/non-high vacuum treated) sample of boronium IL [(1-methylimidazole) (triethylamine)BH$_2$]$^{+1}$ Tf$_2$N$^{-1}$ 2. Peak assignments (left to right) are: imidazole C$^2$—H; imidazole C$^4$—H or C$^5$—H; imidazole C$^5$—H or C$^4$—H; imidazole N-methyl; triethylamine CH$_2$ groups; triethylamine CH$_3$ groups. Though not shown in this spectrum, integrated intensities are 1:1:1:3:6:9. The small peak at 7.26 is residual CHCl$_3$ in the NMR solvent; Trace impurities of 1-methyl imidazole and diethyl ether are also present, these materials being subsequently removed under high vacuum. Note the quite high level of purity achieved in the crude reaction product. The barely perceptible, broad rise in the baseline from around 2 ppm to just past 3 ppm is from the BH$_2$ group. Also note the unusually high-field chemical shifts for the imidazolium ring protons; Tf$_2$N$^-$ salts of "conventional" imidazolium ions would have these resonances offset to lower field by 0.5-1.0 ppm.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A salt represented by formula I:

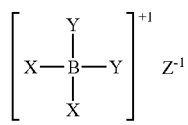

wherein, independently for each occurrence,

X is —NR$^A$(R$^B$)$_2$ or an optionally substituted heterocycle selected from the consisting of pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium and diazepinium;

Y is hydrogen;

Z$^{-1}$ is boron tetraphenyl, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide;

R$^A$ is hydrogen, alkyl, fluoroalkyl, cycloalkyl, aryl, heteroaryl, aralkyl, heteroaralkyl or —[C(R$^C$)$_2$]$_p$—R$^D$;

R$^B$ is alkyl, fluoroalkyl, cycloalkyl, aryl, heteroaryl, aralkyl, heteroaralkyl or —[C(R$^C$)$_2$]$_p$—R$^D$;

R$^C$ is hydrogen, halogen, alkyl, fluoroalkyl, cycloalkyl, heterocycloalkyl, alkenyl, cycloalkenyl, heterocycloalkenyl, alkynyl, aryl, heteroaryl, aralkyl or heteroaralkyl;

R$^D$ is hydrogen, halogen, alkyl, fluoroalkyl, cycloalkyl, heterocycloalkyl, cycloalkenyl, heterocycloalkenyl, aryl, heteroaryl, —OR$^C$, —N(R$^C$)$_2$, —SR$^C$, —C(=O)OR$^C$, —C(=O)N(R$^C$)$_2$, —OC(=O)R$^C$, —NR$^C$C(=O)R$^C$, —C(=O)N(R$^C$)$_2$, —C(=O)SR$^C$, —SC(=O)R$^C$, —S(=O)R$^C$, —S(=O)$_2$R$^C$, —S(=O)$_2$OR$^C$, —C(=O)R$^C$, —C(=NR$^C$)R$^C$, —C(=S)R$^C$, —C(R$^C$)=C(R$^C$)$_2$, —C≡CR$^C$ or —[C(R$^C$)$_2$]$_p$—R$^C$;

p is 1-10 inclusive;

optionally two instances of X, taken with the boron to which they are bound, form an optionally substituted 5-, 6-, 7- or 8-membered ring;

optionally two instances of R$^B$, taken together with the nitrogen to which they are bound, form an optionally substituted 5-, 6-, 7- or 8-membered ring; and optionally R$^A$ and two instances of R$^B$, taken together with the nitrogen to which they are bound, for an optionally substituted 5-, 6-, 7-, 8-membered bicyclo-ring;

provided that the salt of formula I has a melting point less than or equal to about 100° C.

2. The salt of claim 1, wherein at least one of said optionally substituted heterocycles is bonded to boron through a heteroatom.

3. The salt of claim 1, wherein X is —NR$^A$(R$^B$)$_2$ or an optionally substituted heterocycle selected from the consisting of imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium and diazepinium.

4. The salt of claim 1, wherein said optionally substituted heterocycle is optionally substituted with one or more substituents selected from the group consisting of halogen, alkyl, fluoroalkyl, cycloalkyl, heterocycloalkyl, cycloalkenyl, heterocycloalkenyl, aryl, heteroaryl, —OR$^C$, —N(R$^C$)$_2$, —SR$^C$, —C(=O)OR$^C$, —OC(=O)R$^C$, —NR$^C$C(=O)R$^C$, —C(=O)N(R$^C$)$_2$, —C(=O)SR$^C$, —SC(=O)R$^C$, —S(=O)R$^C$, —S(=O)$_2$R$^C$, —S(=O)$_2$OR$^C$, —C(=O)R$^C$, —C(=NR$^C$)R$^C$, —C(=S)R$^C$, —C(R$^C$)=C(R$^C$)$_2$, —C≡CR$^C$ and —[C(R$^C$)$_2$]$_p$—R$^D$.

5. The salt of claim 1, wherein said optionally substituted heterocycle is optionally substituted with one or more groups selected from the group consisting of alkyl and fluoroalkyl.

6. The salt of claim 1, wherein Z$^{-1}$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide or bis(p-toluenesulfonyl)amide.

7. The salt of claim 1, wherein Z$^{-1}$ represents bis(methanesulfonyl)amide, bis(trifluoromethanesulfonyl)amide, bis(benzenesulfonyl)amide or bis(p-toluenesulfonyl)amide.

8. The salt of claim 1, wherein Z$^{-1}$ represents bis(trifluoromethanesulfonyl)amide or (trifluoromethanesulfonyl)(trifluoroacetyl)amide.

9. The salt of claim 1, provided that the salt of formula I has a melting point less than or equal to about 45° C.

10. The salt of claim 1, provided that the salt of formula I has a melting point less than or equal to about 25° C.

11. A salt represented by formula IV, V, or VI:

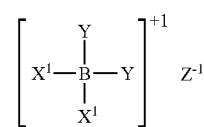

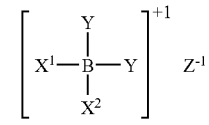

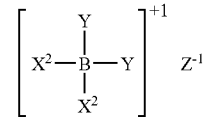

wherein, independently for each occurrence,

X$^1$ is —NR$^A$(R$^B$)$_2$;

X$^2$ is an optionally substituted heterocycle selected from the group consisting of pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium and diazepinium;

Y is hydrogen;

Z$^{-1}$ is boron tetraphenyl, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide or bis(p-toluenesulfonyl)amide;

$R^A$ is hydrogen, alkyl, fluoroalkyl, cycloalkyl, aryl, heteroaryl, aralkyl, heteroaralkyl or —$[C(R^C)_2]_p$—$R^D$;

$R^B$ is alkyl, fluoroalkyl, cycloalkyl, aryl, heteroaryl, aralkyl, heteroaralkyl or —$[C(R^C)_2]_p$—$R^D$;

$R^C$ is hydrogen, halogen, alkyl, fluoroalkyl, cycloalkyl, heterocycloalkyl, alkenyl, cycloalkenyl, heterocycloalkenyl, alkynyl, aryl, heteroaryl, aralkyl, or heteroaralkyl;

$R^D$ is hydrogen, halogen, alkyl, fluoroalkyl, cycloalkyl, heterocycloalkyl, cycloalkenyl, heterocycloalkenyl, aryl, heteroaryl, —$OR^C$, —$N(R^C)_2$, —$SR^C$, —$C(=O)OR^C$, —$C(O)N(R^C)_2$, —$OC(=O)R^C$, —$NR^C(=O)R^C$, —$C(=O)N(R^C)_2$, —$C(=O)SR^C$, —$SC(=O)R^C$, —$S(=O)R^C$, —$S(=O)_2R^C$, —$S(=O)_2OR^C$, —$C(=O)R^C$, —$C(=NR^C)R^C$, —$C(=S)R^C$, —$C(R^C)=C(R^C)_2$, —$C\equiv CR^C$ or —$[C(R^C)_2]_p$—$R^C$;

p is 1-10 inclusive;

optionally two $X^1$, two $X^2$, and a $X^1$ and an $X^2$, taken together with the boron to which they are bound, form an optionally substituted 5-, 6-, 7- or 8-membered ring;

optionally two instances of $R^B$, taken together with the nitrogen to which they are bound, form an optionally substituted 5-, 6-, 7- or 8-membered ring; and optionally $R^A$ and two instances of $R^B$, taken together with the nitrogen to which they are bound, for an optionally substituted 5-, 6-, 7-, 8-membered bicyclo-ring;

provided that the salt of formula VI, V, or VI has a melting point less than or equal to about 100° C.

12. The salt of claim 11, wherein at least one of said optionally substituted heterocycles is bonded to boron through a heteroatom.

13. The salt of claim 11, wherein X is —$NR^A(R^B)_2$ or an optionally substituted heterocycle selected from the consisting of imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium and diazepinium.

14. The salt of claim 11, wherein said optionally substituted heterocycle is optionally substituted with one or more substituents selected from the group consisting of halogen, alkyl, fluoroalkyl, cycloalkyl, heterocycloalkyl, cycloalkenyl, heterocycloalkenyl, aryl, heteroaryl, —$OR^C$, —$N(R^C)_2$, —$SR^C$, —$C(=O)OR^C$, —$OC(O)R^C$, —$NR^C(=O)R^C$, —$C(=O)N(R^C)_2$, —$C(=O)SR^C$, —$SC(=O)R^C$, —$S(=O)R^C$, —$S(=O)_2R^C$, —$S(=O)_2OR^C$, —$C(=O)R^C$, —$C(=NR^C)R^C$, —$C(=S)R^C$, —$C(R^C)=C(R^C)_2$, —$C\equiv CR^C$ and —$[C(R^C)_2]_p$—$R^D$.

15. The salt of claim 11, wherein said optionally substituted heterocycle is optionally substituted with one or more groups selected from the group consisting of alkyl and fluoroalkyl.

16. The salt of claim 11, wherein $R^A$ is alkyl, fluoroalkyl, cycloalkyl, aryl, heteroaryl, aralkyl, heteroaralkyl or —$[C(R^C)_2]_p$—$R^D$.

17. The salt of claim 11, wherein $R^A$ is alkyl.

18. The salt of claim 11, wherein $R^A$ is alkyl.

19. The salt of claim 11, wherein $R^A$ is alkyl; and $R^B$ is alkyl.

20. The salt of claim 11, wherein $Z^{-1}$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide or bis(p-toluenesulfonyl)amide.

21. The salt of claim 11, wherein $Z^{-1}$ represents bis(methanesulfonyl)amide, bis(trifluoromethanesulfonyl)amide, bis(benzenesulfonyl)amide or bis(p-toluenesulfonyl)amide.

22. The salt of claim 11, wherein $Z^{-1}$ represents bis(trifluoromethanesulfonyl)amide or (trifluoromethanesulfonyl)(trifluoroacetyl)amide.

23. The salt of claim 11, provided that the salt of formula VI, V, or VI has a melting point less than or equal to about 45° C.

24. The salt of claim 11, provided that the salt of formula VI, V, or VI has a melting point less than or equal to about 25° C.

25. A salt represented by formula VII or VIII:

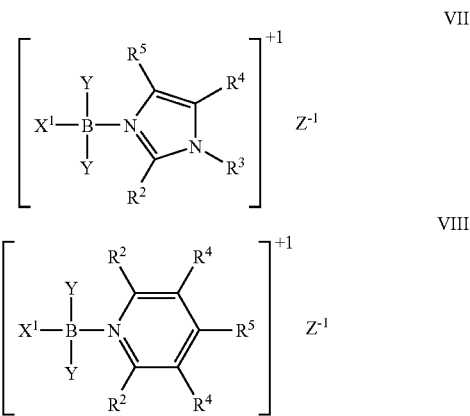

wherein, independently for each occurrence, $X^1$ is —$NR^A(R^B)_2$; or an optionally substituted heterocycle selected from the group consisting of pyridinium and imidazolium;

Y is hydrogen;

$Z^{-1}$ is boron tetraphenyl, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide or bis(p-toluenesulfonyl)amide;

$R^A$ is hydrogen, alkyl, fluoroalkyl, cycloalkyl, aryl, heteroaryl, aralkyl, heteroaralkyl or —$[C(R^C)_2]_p$—$R^D$;

$R^B$ is alkyl, fluoroalkyl, cycloalkyl, aryl, heteroaryl, aralkyl, heteroaralkyl or —$[C(R^C)_2]_p$—$R^D$;

$R^C$ is hydrogen, halogen, alkyl, fluoroalkyl, cycloalkyl, heterocycloalkyl, alkenyl, cycloalkenyl, heterocycloalkenyl, alkynyl, aryl, heteroaryl, aralkyl or heteroaralkyl;

$R^D$ is hydrogen, halogen, alkyl, fluoroalkyl, cycloalkyl, heterocycloalkyl, cycloalkenyl, heterocycloalkenyl, aryl, heteroaryl, —$OR^C$, —$N(R^C)_2$, —$SR^C$, —$C(=O)OR^C$, —$C(O)N(R^C)_2$, —$OC(=O)R^C$, —$NR^C(=O)R^C$, —$C(=O)N(R^C)_2$, —$C(=O)SR^C$, —$SC(=O)R^C$, —$S(=O)R^C$, —$S(=O)_2R^C$, —$S(=O)_2OR^C$, —$C(=O)R^C$, —$C(=NR^C)R^C$, —$C(=S)R^C$, —$C(R^C)=C(R^C)_2$, —$C\equiv CR^C$ or —$[C(R^C)_2]_p$—$R^C$;

$R^2$ is hydrogen, halogen, alkyl, fluoroalkyl, cycloalkyl, heterocycloalkyl, cycloalkenyl, heterocycloalkenyl, aryl, heteroaryl, —$OR^C$, —$N(R^C)_2$, —$SR^C$, —$C(=O)OR^C$, —$OC(=O)R^C$, —$NR^CC(=O)R^C$, —$C(=O)N(R^C)_2$, —C(=O)SR$^C$, —SC(=O)R$^C$, —S(=O)R$^C$, —S(=O)$_2$R$^C$, —S(=O)$_2$OR$^C$, —C(=O)R$^C$, —C(=NR$^C$)R$^C$, —C(=S)R$^C$, —C(R$^C$)=C(R$^C$)$_2$, —C≡CR$^C$ or —[C(R$^C$)$_2$]$_p$—R$^D$;

R$^3$ is hydrogen, alkyl, fluoroalkyl, cycloalkyl, aryl, heteroaryl, aralkyl, heteroaralkyl or —[C(R$^C$)$_2$]$_p$—R$^D$;

R$^4$ is hydrogen, halogen, alkyl, fluoroalkyl, cycloalkyl, heterocycloalkyl, cycloalkenyl, heterocycloalkenyl, aryl, heteroaryl, —OR$^C$, —N(R$^C$)$_2$, —SR$^C$, —C(=O)OR$^C$, —OC(=O)R$^C$, —NR$^C$C(=O)R$^C$, —C(=O)N(R$^C$)$_2$, —C(=O)SR$^C$, —SC(=O)R$^C$, —S(=O)R$^C$, —S(=O)$_2$R$^C$, —S(=O)$_2$OR$^C$, —C(=O)R$^C$, —C(=NR$^C$)R$^C$, —C(=S)R$^C$, —C(R$^C$)=C(R$^C$)$_2$, —C≡CR$^C$ or —[C(R$^C$)$_2$]$_p$—R$^D$;

R$^5$ is hydrogen, halogen, alkyl, fluoroalkyl, cycloalkyl, heterocycloalkyl, cycloalkenyl, heterocycloalkenyl, aryl, heteroaryl, —OR$^C$, —N(R$^C$)$_2$, —SR$^C$, —C(=O)OR$^C$, —OC(=O)R$^C$, —NR$^C$C(=O)R$^C$, —C(=O)N(R$^C$)$_2$, —C(=O)SR$^C$, —SC(=O)R$^C$, —S(=O)R$^C$, —S(=O)$_2$R$^C$, —S(=O)$_2$OR$^C$, —C(=O)R$^C$, —C(=NR$^C$)R$^C$, —C(=S)R$^C$, —C(R$^C$)=C(R$^C$)$_2$, —C≡CR$^C$ or —[C(R$^C$)$_2$]$_p$—R$^D$;

optionally two instances of R$^B$, taken together with the nitrogen to which they are bound, form an optionally substituted 5-, 6-, 7- or 8-membered ring; and optionally R$^A$ and two instances of R$^B$, taken together with the nitrogen to which they are bound, for an optionally substituted 5-, 6-, 7-, 8-membered bicyclo-ring; and p is 1-10 inclusive;

provided that the salt of formula VII or VIII has a melting point less than or equal to about 100° C.

26. The salt of claim 25, wherein R$^A$ is alkyl, fluoroalkyl, cycloalkyl, aryl, heteroaryl, aralkyl, heteroaralkyl or —[C(R$^C$)$_2$]$_p$—R$^D$.

27. The salt of claim 25, wherein R$^A$ is alkyl.

28. The salt of claim 25, wherein R$^B$ is alkyl.

29. The salt of claim 25, wherein R$^A$ is alkyl; and R$^B$ is alkyl.

30. The salt of claim 25, wherein R$^2$ is hydrogen or alkyl.

31. The salt of claim 25, wherein R$^3$ is alkyl.

32. The salt of claim 25, wherein R$^4$ is hydrogen or alkyl.

33. The salt of claim 25, wherein R$^5$ is hydrogen or alkyl.

34. The salt of claim 25, wherein R$^2$ is hydrogen or alkyl; R$^3$ is alkyl; R$^4$ is hydrogen or alkyl; and R$^5$ is hydrogen or alkyl.

35. The salt of claim 25, wherein Z$^{-1}$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide or bis(p-toluenesulfonyl)amide.

36. The salt of claim 25, wherein Z$^{-1}$ represents bis(methanesulfonyl)amide, bis(trifluoromethanesulfonyl)amide, bis(benzenesulfonyl)amide or bis(p-toluenesulfonyl)amide.

37. The salt of claim 25, wherein Z$^{-1}$ represents bis(trifluoromethanesulfonyl)amide or (trifluoromethanesulfonyl)(trifluoroacetyl)amide.

38. The salt of claim 25, provided that the salt of formula VII or VIII has a melting point less than or equal to about 45° C.

39. The salt of claim 25, provided that the salt of formula VII or VIII has a melting point less than or equal to about 25° C.

40. A salt selected from the group consisting of:

[(N-1-methylimidazole)(trimethylamine)BH$_2$]$^{+1}$Tf$_2$N$^{-1}$,

[(N-1-methylimidazole)(triethylamine)BH$_2$]$^{+1}$Tf$_2$N$^{-1}$,

[(N-1-methylimidazole)(di(n-butyl)methylamine)BH$_2$]$^{+1}$Tf$_2$N$^{-1}$,

[(N-1-butylimidazole)(trimethylamine)BH$_2$]$^{+1}$Tf$_2$N$^{-1}$,

[(N-1-butylimidazole)(triethylamine)BH$_2$]$^{+1}$Tf$_2$N$^{-1}$,

[(N-1-butylimidazole)(quinuclidine)BH$_2$]$^{+1}$Tf$_2$N$^{-1}$,

[(N-1,2-dimethylimidazole)(trimethylamine)BH$_2$]$^{+1}$Tf$_2$N$^{-1}$ and

[(N-1-decyl-2-methylimidazole)(trimethylamine)BH$_2$]$^{+1}$Tf$_2$N$^{-1}$.

* * * * *